(12) United States Patent
Ruf et al.

(10) Patent No.: US 8,637,300 B2
(45) Date of Patent: Jan. 28, 2014

(54) MAGNETIC GLASS PARTICLES FOR USE IN BIOGAS PLANTS, FERMENTATION AND SEPARATION PROCESSES

(71) Applicant: Sued-Chemie IP GmbH & Co. KG, Munich (DE)

(72) Inventors: Friedrich Ruf, Tiefenbach-Ast (DE); Ulrich Sohling, Freising (DE); Elisabeth Neitmann, Moosburg (DE); Bernd Linke, Potsdam (DE); Jan Mumme, Potsdam (DE); Patrice Ramm, Berlin (DE); Oliver Menhorn, Nuremberg (DE); Karl Weinberger, Bischofsmais (DE); Peter Kumpf, Luetzelbach (DE)

(73) Assignee: SUED-Chemie IP GmbH & Co. KG, Munich (DE)

( * ) Notice: Subject to any disclaimer, the term of this patent is extended or adjusted under 35 U.S.C. 154(b) by 0 days.

(21) Appl. No.: 13/763,331

(22) Filed: Feb. 8, 2013

(65) Prior Publication Data
US 2013/0224823 A1    Aug. 29, 2013

Related U.S. Application Data

(63) Continuation of application No. PCT/EP2011/063930, filed on Aug. 12, 2011.

(30) Foreign Application Priority Data

Aug. 12, 2010   (DE) .......................... 10 2010 034 083

(51) Int. Cl.
*A62D 3/02* (2007.01)
*C12N 11/14* (2006.01)

(52) U.S. Cl.
USPC ........................................ 435/262.5; 435/176

(58) Field of Classification Search
USPC ................................................ 435/262.5, 176
See application file for complete search history.

(56) References Cited

U.S. PATENT DOCUMENTS

| | | | |
|---|---|---|---|
| 4,233,169 A | 11/1980 | Beall et al. | |
| 4,735,725 A | 4/1988 | Reischl et al. | |

(Continued)

FOREIGN PATENT DOCUMENTS

| | | |
|---|---|---|
| DE | 195 31 801 A1 | 3/1997 |
| DE | 197 34 791 A1 | 2/1999 |

(Continued)

OTHER PUBLICATIONS

Berensmeier "Magnetic particles for the separation and purification of nucleic acids," Appl Microbiol Biotechnol 73:495-504,2006.*

(Continued)

*Primary Examiner* — Rosanne Kosson
*Assistant Examiner* — Larry Moore
(74) *Attorney, Agent, or Firm* — Walter Ottesen P.A.

(57) ABSTRACT

A method for treating an organic and/or inorganic substrate utilizing a granular material made of a solid foam as support for an active component, for example a biocatalyst such as a microorganism or an enzyme. The solid foam has a continuous phase in which magnetizable particles are embedded, such that the support with the biologically active component immobilized thereon can be separated from a mixture with a magnetic separation device.

11 Claims, 15 Drawing Sheets

(56) References Cited

U.S. PATENT DOCUMENTS

| | | | |
|---|---|---|---|
| 5,000,853 | A | 3/1991 | Reischl et al. |
| 5,601,979 | A | 2/1997 | Wong |
| 5,610,274 | A | 3/1997 | Wong |
| 5,734,020 | A | 3/1998 | Wong |
| 6,043,068 | A * | 3/2000 | Maekawa et al. ............ 435/182 |
| 6,255,477 | B1 | 7/2001 | Kleiber et al. |
| 6,870,047 | B2 | 3/2005 | Kleiber et al. |
| 7,183,002 | B2 * | 2/2007 | Sauer et al. .................. 428/404 |
| 7,922,917 | B2 | 4/2011 | Sauer et al. |
| 8,202,427 | B2 | 6/2012 | Sauer et al. |
| 2007/0104949 | A1 | 5/2007 | Bunge |
| 2007/0186587 | A1 | 8/2007 | Dennert |
| 2008/0156038 | A1 | 7/2008 | Dennert |
| 2009/0305377 | A1 | 12/2009 | Mumme et al. |

FOREIGN PATENT DOCUMENTS

| | | |
|---|---|---|
| DE | 198 17 268 A1 | 10/1999 |
| DE | 10 2005 024 886 B3 | 12/2006 |
| EP | 1 900 697 A1 | 3/2008 |
| EP | 1 900 698 A1 | 3/2008 |
| EP | 2 022 768 A2 | 2/2009 |
| JP | 61-48441 A | 3/1986 |

OTHER PUBLICATIONS

Klose, S. et al, "Stratigraphic Distribution of Lignite-Derived Atmospheric Deposits in Forest Soils of the Upper Lusatian Region, East Germany", Water, Air, and Soil Pollution, 142: pp. 3 to 25, 2003, Kluwer Academic Publishers, Netherlands.

Liao, M. et al, "Fast and efficient adsorption/desorption of protein by a novel magnetic nano-adsorbent", Biotechnology Letters 24: pp. 1913 to 1917, 2002, Kluwer Academic Publishers, Netherlands.

Soares, A. et al, "Biodegradation of nonylphenol in a continuous packed-bed bioreactor", Biotechnology Letters 25: pp. 927 to 933, 2003, Kluwer Academic publishers, Netherlands.

Tong, X. et al, "A Novel Magnetic Affinity Support for Protein Adsorption and Purification", Biotechnol. Prog. 2001, 17, pp. 134 to 139, American Chemical Society and American Institute of Chemical Engineers.

Zilouei, H. et al, "Biological degradation of chlorophenols in packed-bed bioreactors using mixed bacterial consortia", Process Biochemistry 41 (2006) pp. 1083 to 1089, Elsevier.

International Search Report dated Jan. 23, 2012 of international application PCT/EP2011/063930 on which this application is based.

* cited by examiner

MAGNETIC GLASS PARTICLES FOR USE IN BIOGAS PLANTS, FERMENTATION AND SEPARATION PROCESSES

CROSS REFERENCE TO RELATED APPLICATIONS

This application is a continuation application of international patent application PCT/EP2011/063930, filed Aug. 12, 2011, designating the United States and claiming priority from German application 10 2010 034 083.9, filed Aug. 12, 2010, and the entire content of both applications is incorporated herein by reference.

FIELD OF THE INVENTION

The invention relates to a method for treating an organic and/or inorganic substrate, a magnetizable aggregate as is used in the method for treating an organic substrate, as well as a method for producing such a magnetizable aggregate.

BACKGROUND OF THE INVENTION

Fermentations have already been used for a very long time to preserve foodstuffs for example. For this, either microorganisms are used, for example in the production of wine and beer or in the production of yoghurt and kefir, or enzymes direct, for example when souring milk using rennet. Fermentations can proceed under both aerobic and anaerobic conditions. A fermentation under anaerobic conditions is also called anaerobic fermentation. Fermentations are also used in the industrial-scale production of chemicals, for example in the production of citric acid or in the production of medicinal products such as antibiotics or insulin. A large number of reactors and procedures have been developed for these industrial processes. Thus the processes can be carried out continuously or batch-wise. With the reactors, types have been developed in which the microorganisms or the enzyme are arranged stationary in a reactor, for example in a packed bed, over which the substrate is then passed in liquid form. However, processes in which the microorganisms or the enzyme are distributed homogenously in the substrate are also known. The microorganisms or the enzyme can be immobilized on a solid support which is distributed in the substrate. However, a support is not necessary in many reactions.

The organic substrates that are used in such fermentations can vary greatly. For example, an aqueous glucose solution can be used as a basis, which serves as substrate or energy source for the microorganism during production of the desired substance. The organic substrate can be homogeneous and present for example as a solution. With other technical fermentations very heterogeneous organic substrates are used. For example in biogas production substrates are used which can also comprise solid constituents, wherein these solid constituents can also be present in the form of relatively large pieces. Typical organic substrates as used in biogas production are for example animal manure which can also be mixed with litter, plant chaff or sewage sludge.

Various microorganisms, for example bacteria, fungi or also cell cultures, are used for fermentations. If a fermentation is carried out with the help of microorganisms, in one variant of the procedure firstly the microorganisms can colonize the organic substrate. For this, in a start-up phase of the bioreactor the substrate is firstly seeded with the relevant microorganism, which then multiplies, accompanied by reaction of the organic substrate, and colonizes the organic substrate.

However, microorganisms as well as reactions catalyzed by same are also known in which the substrate is not colonized by the microorganisms. With this method variant of a fermentation, the microorganisms float in a nutrient solution and absorb dissolved nutrients via the surface. The microorganisms can have previously secreted enzymes in order, for example, to decompose solid substrates into smaller water-soluble components.

If the process is to be carried out continuously, fresh organic substrate is channelled into the reaction chamber of the reactor during the fermentation, while a corresponding quantity of spent substrate is discharged from the reactor. Microorganisms are also removed from the reaction chamber with the discharged spent substrate. This loss of microorganisms must be compensated by a corresponding growth. In particular with slow-growing organisms the growth rate can be the limiting factor for the capacity of the reactor. Below a critical value at which the quantity of renewable microorganisms is greater than the quantity of microorganisms discharged with the spent substrate, there is always a sufficient quantity of microorganisms available to sustain the fermentation. Then, for example, the quantity of fed organic substrate can form the limiting factor. If the quantity of fed organic substrate is further increased, a critical value is reached at which the quantity of renewable microorganisms corresponds to the quantity of microorganisms discharged with the spent substrate. The fermentation in the reaction chamber then proceeds in a stable manner. With a further increase in the quantity of fed substrate the renewable quantity of microorganisms can no longer compensate the loss in microorganisms discharged with the spent substrate. The microorganisms content of the reactor then falls constantly with the result that the fermentation no longer proceeds in a stable manner. The performance of the reactor and thus the yield of product decrease with a further increase in the quantity of fed substrate until fermentation finally stops.

An example of a fermentation with very slow-growing microorganisms is biogas production. During the production of biogas, in the final step with the help of methanogenic bacteria, methane is produced from $H_2$ and $CO_2$ or from ethyl acetate or other low-molecular compounds such as methylamine. This reaction takes place under strict anaerobic and reductive conditions. For thermodynamic reasons, methanogenic bacteria can achieve only an extremely small energy gain per reacted substrate molecule. Long generation times are therefore a necessary and inevitable consequence. For this reason, the start-up phase of newly charged biogas reactors also lasts a long time. Once a biogas reactor has finally reached its operational state, the growth rate of the slowest-growing microorganisms determines the maximum possible throughput of organic substrate.

In order, for a given reactor, to increase the throughput rate and thus the capacity of the reactor, the stationary concentration of microorganisms in the reactor must be increased. This can take place within a very limited framework by optimizing process parameters. A further possibility for increasing the stationary quantity of microorganisms in the reaction chamber of the bioreactor is to recover the microorganisms from the discharged digestate and return them to the reaction chamber again. However, as the digestate is very heterogeneous in composition, the microorganisms can be separated from the digestate only with great difficulty.

A method is described in DE 10 2005 024 886 B3 in which magnetizable particles are added to the organic substrate. The microorganisms are present in the reaction chamber or in the organic substrate in the form of bacterial floc. The bacteria are surrounded by a layer of slime which makes possible a cohesion between the individual bacteria and the composition of larger aggregates. Magnetizable particles can be embedded in the slime separated from the microorganisms, whereby a force exerted on the magnetizable particles can be transferred onto the microorganisms. It was able to be shown that it is possible to separate the microorganisms from the digestate by passing the digestate past a stationary magnet. A separation tube, to the outside of which permanent magnets are attached, can be provided for this. If the digestate is passed through the separation tube the stationary magnet attracts the magnetizable particles enclosed in the bacteria slime, whereby the bacterial floc in the digestate is moved towards the magnet and deposited on the wall of the separation tube. If the permanent magnets are removed from the outer wall of the separation tube, the layer of microorganisms deposited on the inner wall of the separation tube can be flushed out of the tube. The collected microorganisms can then be returned to the reactor again.

Through the method described in DE 10 2005 024 886 B3 it was able to be shown that the separation of microorganisms with the help of magnetizable particles is possible. However, the method does not yet make possible such a high degree of separation that the method can be used profitably in industrial plants. The ferrite used in the method is used in very fine-particle form, with the result that its sedimentation rate is low and the particles can be enclosed in the layer of slime of the bacteria. These very small magnetizable particles move only very slowly in the applied magnetic field because of the viscosity of the water and the weak magnetic forces. If it is attempted to improve the separation rate of the magnetizable particles by increasing the force exerted by the magnets, the danger is that the magnetizable particles will be pulled out of the slime layer of the microorganism floc. It is then no longer possible to separate the bacterial floc from the digestate. If it is attempted to improve the separation rate by using larger magnetizable particles, these larger particles can be colonized by microorganisms, whereby the bonding of the microorganisms to the magnetizable particles improves. However, the problem then occurs that the sedimentation rate of the magnetizable particles is very high. The particles are then no longer distributed homogeneously in the organic substrate during the fermentation, i.e. the fermentation can be carried out uniformly in the whole reaction chamber only with considerable outlay.

The possibility of accumulating substances or microorganisms with the help of magnetizable particles from a mixture of substances has already been shown using various examples. However, these applications relate mostly only to the separation of very small quantities of substance, for example in use in test kits. The use of magnetizable particles then makes it possible to avoid a laborious separation by centrifuging.

Thus highly porous ferromagnetic or ferrimagnetic glass particles that contain iron oxide or iron-containing pigments are described in U.S. Pat. No. 8,202,427; U.S. Pat. No. 7,922,917; and, U.S. Pat. No. 7,183,002. The glass particles preferably have a diameter of 5 to 25 µm, particular preferably 7 to 10 µm. To produce the glass particles firstly a suspension of the magnetizable particles in for example glycerol or glycol is produced. A hydrolyzable silicon compound, for example a tetraalkoxy silane, is then added to this suspension. The silicon compound is then hydrolyzed with an alkaline or acidic buffer with the result that $SiO_2$ deposits on the magnetizable particles and an open-pore structure forms. The particles are separated off and dried below the Curie temperature, preferably in the range of from 100 to 500° C. The glass particles can be used to accumulate a specific substance, for example a protein, from a sample mixture. For this the porous glass particle, the surface of which has optionally been modified by providing suitable groups in order to increase the affinity between the substance and the surface of the glass particle, is mixed with the sample mixture. The substance contained in the mixture is adsorbed on the surface of the magnetizable glass particles. By applying an external magnetic field the porous glass particles can be deposited together with the molecules of interest adsorbed on same for example on the wall of a sample vessel. The liquid phase can then be separated off very easily, with the result that only the magnetizable glass particles with the substance adsorbed thereon remain in the sample vessel.

M.-H. Liao, B.-H. Chen, Biotechnology Letters 24, 1913-1917, 2002 describe a magnetizable adsorbent which for example can be used to accumulate a protein from a solution. For this, nanoparticles from superparamagnetic $Fe_3O_4$ are coated with a covalently bonded layer of polyacrylic acid. The polyacrylate has a large number of ionic groups which can interact with the protein of interest, whereby the protein is bonded to the surface of the nanoparticle. The polyacrylate chains are bonded to the $Fe_3O_4$ nanoparticle by activation with carbodiimide. On average two polyacrylate molecules are bonded per magnetic nanoparticle.

X.-D. Tong, B. Xue, Y. Sun, Biotechnol. Prog. 2001, 17, 134-139 describe a magnetizable support which can be used for the adsorption of proteins as well as their accumulation. The magnetizable particles have a core of a magnetizable material, for example $Fe_3O_4$, which is coated with a shell of cross-linked polyvinyl alcohol. In order to increase the affinity of the particles for proteins, the surface can be modified by bonding corresponding groups to the surface of the particle.

In addition to the above-described magnetizable particles, a whole series of other supports are known for carrying out fermentations or accumulating proteins. Thus A. Soares, B. Guieysse, B. Mattiasson, Biotechnology Letters 25, 927-933, 2003 describe the biological degradation of nonylphenol in a continuously operated fixed bed bioreactor. The bed consists of a granular material of foam glass, wherein a biofilm of microorganisms is immobilized on the surface of the grains of the granular material. The substrate charged with nonylphenol is passed over the bed, wherein a clear degradation of the nonylphenol can be detected in the eluate removed from the reactor.

H. Zilouei, B. Guieysse, B. Mattiasson, Process Biochemistry 41 (2006), 1083-1089 describe the biological degradation of chlorophenols with the help of bacteria that are immobilized as biofilm in a packed bed of foam-glass granular material. Also here it was able to be shown that a clear degradation of the chlorophenols can be achieved if a substrate charged with chlorophenol is passed through the packed reactor.

Foam-glass granular materials are available on the market in various forms. The foam-glass granular materials can have an open-pore or a closed-pore structure. Moreover the granular materials can be produced from various types of glass. For example the strength and temperature resistance of the glass granular material can be increased by adding $Al_2O_3$.

The production of an open-pore foam-glass granular material is described in DE 195 31 801 A1. For this, a glass powder is mixed with a silicon organic compound as well as wax microspheres. This mixture is processed to a granular material which is firstly prehardened at a low temperature. A cohesion between the particles of the glass powder is thus produced by partial decomposition of the silicon organic compound. Then the wax is melted out by further increasing the temperature, with the result that open pores remain in the granular material. After the wax has been melted out the glass granular material is hardened at a higher temperature, preferably in the range of from 600 to 800° C. The open-pore glass granular material is suitable for immobilizing microorganisms which for example are used in aerobic waste-water treatment.

Likewise an open-pore foam-glass granular material which is produced from a glass powder mixture with a low-melting and a high-melting component is used in DE 197 34 791 A1. The glass powder mixture is mixed with a blowing agent and then heated above the blowing temperature of the low-melting glass component. The walls of the pores, which are constructed from the low-melting component, open during blowing, with the result that an open-pore structure is obtained.

This open-pore foam-glass granular material can also be used as a support for microorganisms for the aerobic treatment of waste waters as described in DE 198 17 268 A1. For this the open-pore foam-glass granular material is coated firstly with approximately 5 mass-% $Fe_2O_3$ by dipping the granular material into an iron salt solution and then tempering it. The granular material can then be fed into an activated sludge reactor. Through the iron oxide, poorly degradable compounds are pre-oxidized by the addition of hydrogen peroxide, while the further mineralization of microorganisms is effected.

Magnetizable foam-glass granular materials have also already been described. Thus foam glasses in which ferromagnetic substances, such as for example iron, nickel or cobalt, are homogenously distributed in the glass foam, are known from EP 1 900 698 A1 and EP 1 900 697 A1. By foam glass is meant a solidified glass foam which comprises airtight closed cells. However, the production and the structure of the magnetizable glass foam are not described. The magnetizable foam glass is used to produce filters. These comprise a liquid-tight casing with foam glass shaped bodies contained therein. The shaped bodies can for example be a granular material with a predetermined or largely arbitrary granulation.

A further open-pore magnetizable inorganic material is described in U.S. Pat. No. 5,734,020. The porous glass is impregnated with a suspension of metallic particles to produce the material. Excess suspension is removed and the impregnated particles then dried. As the magnetizable particles are deposited in the pores of the glass foam, the pore volume of the glass decreases due to the impregnation. The granular material has a grain size in the range of from approximately 1 to 200 μm. It can be used as support for chromatographic processes, in immunoassays, for syntheses, for example of oligonucleotides, as well as other separating and purifying processes.

A granular material made of fragments of a sinter body sintered from ground blow-moulded glass in which iron particles are embedded is described in US2007/0104949. The sinter body is broken into a granular material with the result that a large surface area is obtained, wherein the iron particles protrude from the surface. The granular material is produced according to a specific embodiment by firstly mixing glass powder with a blowing agent and fine-particle iron and then blowing the mixture, wherein a body, for example in the form of a plate, is obtained. The plate is then broken down into a granular material. The granular material can be magnetically influenced with an iron content of 6 wt.-% and above. This can be used for example to separate off fine particles of the foam glass from a suspension of contaminants. The granular material can be used in particular as feedstock for water purification.

A method for producing foam-glass granular material which is suitable for example as additive for construction materials, to increase the insulating effect of for example walls, is described in US2007/0186587. To produce the foam-glass granular material, firstly pre-ground glass is mixed with water glass and blowing agent accompanied by the addition of water to form a crude mixture. The crude mixture is then wet-ground over several hours to form a slip. The slip is granulated to form granular material green bodies and these are foamed in rotary kilns at a temperature of usually 800 to 900° C.

A porous material which has a content of silicon oxide in a range of from 60 wt.-% to 85 wt.-%, aluminium oxide in a range of from 6 wt.-% to 20 wt.-% and alkaline- and/or alkaline-earth oxide and/or alkaline- and/or alkaline-earth hydroxide in a range of from 0 to 15 wt.-% is described in EP 2 022 768 A2. The surface of the porous material is surrounded by a skin which is preferably water-tight. The water absorptivity according to DIN EN 1609 is between 0 to 5 wt.-%, preferably 0.2 to 3 wt.-%, particularly preferably 0.5 to 1 wt.-%. The foam glass is produced by mixing clay, silicon oxide as well as optionally alkaline- and/or alkaline-earth oxide or alkaline- and/or alkaline-earth hydroxide with water to form a suspension. The suspension is granulated and the granular material optionally dried. The granular material is then heated, wherein a closed-pore porous material is obtained. In order to support the foaming, optionally a blowing agent can also be added to the suspension. Various fields of application are proposed for the foam-glass granular material, for example as thickener, thermal insulation material, sound-absorbing material, filler, construction material, fire-protection agent, refractory material, chromatography material and/or support material.

A further method for producing foam-glass granular material is described in US2008/0156038. Firstly a glass binder slop is produced from water, a propellant and a glass binder at room temperature. Glass powder is then added to the glass binder slop with the result that a moister, more stirrable glass mixture is obtained. The glass mixture is homogenized and then stirred for 2 to 6 hours to at least partly decompose the glass constituents. Further glass powder is then added and the mixture is granulated. The granular material is firstly dried and then foamed at a temperature of approximately 790° C.

As already explained, fermentations can be used for the production of a large number of compounds.

These can be relatively simple compounds such as methane but also compounds with very complex structure, such as for example in the production of medicinal products. The biocatalysts used in fermentations, such as enzymes or microorganisms, can be very valuable, whether they can be made available only at great cost or can be provided in a reactor only in a limited quantity, for example depending on the slow growth rate of a microorganism.

A further field in which great advantages can be expected if biologically active molecules that are accessible only with difficulty can be used repeatedly are separation processes. Capture molecules can be used to accumulate specific components from a solution. For example antibodies, DNA capture probes, RNA capture probes, protein A, avidin, streptavidin or proteins with long histidine chains can be used as capture molecules. Thus far the procedure has been to pass the solution that contains the molecules of interest over a column in which suitable capture molecules are immobilized. However, if the solution contains for example microorganisms, these must be separated off from the solution in advance.

SUMMARY OF THE INVENTION

Therefore, the object of the invention was to make available a method for treating an organic substrate which makes possible the recovery of useful components from the treated organic substrate. The useful component can then be used again or for example also be recycled, in order for example to increase the concentration of biologically active components in a bioreactor.

This object is achieved with a method as disclosed herein. Advantageous embodiments of the method are also disclosed.

With the method according to the invention a special magnetizable particulate support is used which is constructed from a solid foam and on which an active component is immobilized. Magnetizable particles are distributed in the solid phase of the foam, wherein these are enclosed in the continuous phase of the solid foam. As the magnetizable particles are enclosed in the continuous phase, the magnetizable particles are prevented from corroding and thereby losing their magnetizability or being removed from the magnetizable particulate support by for example the particles being dissolved. The magnetizable particles are preferably homogeneously distributed in the solid phase.

The force which a given magnetic field exerts on a support particle can be set by the quantity of the magnetizable material contained in the support and thus the speed influenced with which the support particles are moved in a given magnetic field and a given medium. It is therefore possible to increase the separation rate of the magnetizable support by increasing the quantity of magnetizable material in the support. By increasing the quantity of magnetizable material, the density of the unfoamed granular material increases as, generally, the specific weight of the magnetizable material from which the magnetizable particles are constructed is greater than the density of the solid material of the main phase, for example of a network former or of a glass forming the continuous solid phase of the support. The sedimentation speed of the support in the organic substrate that is provided in the bioreactor would thus increase. However, the sedimentation can be countered by the pore structure of the solid foam.

The solid foam of which the magnetizable support is constructed has, at least in the core of the support, a closed-pore structure. No water or solvent penetrates the closed pores, with the result that they act like a lifting body for the magnetic support in water or another solvent. The density of the support can be set by the pore size or the proportion of pores and the size of the closed-pore core. The degree of foaming can therefore control whether for example the support sinks, floats or, if the support has a density comparable with that of water, remains almost suspended in water.

An active component is immobilized on the magnetizable support. By an active component is meant a component that can interact with the organic and/or inorganic substrate.

The interaction can consist of the organic and/or inorganic substrate being reacted using the immobilized active component. In this embodiment the active component can act for example as catalyst by which the substrate is converted to a product. After the conversion the magnetizable aggregate can be removed from the product mixture and, in a continuously operated process, for example, be added to fresh substrate mixture. However, after the conversion the magnetizable aggregate can also be washed and conditioned in order to be reused again thereafter. Alternatively it can also be stored until it is reused.

According to a preferred embodiment a biocatalytically active system is used as active component. By a biocatalytically active system is meant a system of biological origin which can effect a conversion of an organic and/or inorganic substrate to a product. A system is of biological origin if it occurs in nature or is derived from this, for example with the help of genetic engineering methods. By a biologically active system is meant in particular living cells, parts of cells, for example vesicles, as well as enzymes.

According to an embodiment, living cells can be cells from cell cultures as well as microorganisms. By microorganisms are generally meant microscopically small organisms which can be present preferably as single cells or also multiple cells. According to a preferred embodiment, microorganisms are selected from archaeobacteria, eubacteria, yeasts as well as other fungi. The microorganisms can be used as pure cultures, as defined mixed cultures or even as complex biocoenoses. The microorganisms can be naturally occurring microorganisms or also microorganisms or cells genetically manipulated with known methods.

An interaction between magnetizable aggregate and organic and/or inorganic substrate can, however, for example also be the formation of a preferably non-covalent bond between the substrate and the active component immobilized on the magnetizable support. In this embodiment the magnetizable aggregate can thus adsorb the substrate. This makes possible an embodiment in which the method according to the invention is used for example to accumulate the substrate from a preferably aqueous mixture.

According to one such embodiment the active component is formed by a capture molecule. By a capture molecule is meant a molecule which can bind to a preferably organic substrate by at least one non-covalent bond. The non-covalent bond can be formed by an ionic bond, a dipolar interaction or by van der Waals bonds. Small molecules, for example DNA probes, but also larger biologically active aggregates, for example antibodies, can be used as capture molecules. However, polymers which comprise groups which can form non-covalent bonds to an organic substrate, for example polyethylene imine, can also be used.

The magnetizable aggregate formed from the magnetizable support and the active component immobilized thereon can be distributed very well in liquid media. Therefore it can be used very well in continuous processes in which the magnetizable aggregate is separated off from the product mixture and returned to the process again optionally after an intermediate treatment. If the active component is designed for example as a capture molecule, then the support can for example be added to a culture medium in which a compound of interest is produced in a biologically catalyzed reaction. This compound is then bonded to the magnetizable aggregate via the capture molecule. The magnetizable aggregate with the compound of interest bonded thereto can then be separated from the culture medium with a magnetic separation device and then the compound is displaced again from the magnetizable aggregate or the capture molecule and thus isolated. The magnetizable aggregate depleted of the compound of interest can then be placed back into the culture medium. This method makes it possible to isolate a specific compound continuously from a biologically catalyzed reaction, for example a fermentation, without the process needing to be interrupted or the biological catalyst, e.g. a microorganism, having to be separated off beforehand.

According to an embodiment already named further above the active component is formed as biocatalytically active system. By a biocatalytically active system is meant, within the meaning of the invention, in particular a living cell or a part of a cell or an enzyme which converts an organic and/or inorganic substrate to a product. Substrate and product thus have different structures in this embodiment. The conversion of the substrate can require, for example when using enzymes, the presence of cofactors. The presence of for example nutrients, trace elements and the like can be required when using cells, in particular microorganisms. The conditions for such systems are known per se to a person skilled in the art.

Particularly advantageous results are achieved if the active component or the biocatalytically active system is formed by living cells and in particular by at least one microorganism. The at least one microorganism can belong to an individual species of microorganism. However, it is also possible that several species of microorganism act simultaneously as active component.

As the support is relatively large compared with the magnetizable supports previously used in biological processes, it is not merely integrated in the layer of slime of microorganisms but can be colonized by cells or microorganisms. The microorganisms or cells actively attach themselves to the surface of the support with the help of extracellular polymeric substances. The microorganisms can firstly form colonies on the surface of the support which can combine, upon further growth, to a biofilm. Thereby the density of microorganisms in the substrate is relatively high, with the result that high substrate conversion rates can be realized. The same applies when using cells, for example cells from cell cultures.

In the method according to the invention the support is used in particulate form, i.e. in the form of a pourable granular material.

The particulate magnetizable support with the active component immobilized thereon can be distributed homogeneously in the substrate, which has an advantageous effect on the conversion rate and separation rate respectively, as no local imbalances occur and for example a local hyperacidity can be avoided. Unlike rigid solid beds, there is also no danger of blockage when using particulate supports if the substrate comprises for example solid constituents.

Because of the solid foam structure which is closed-pore at least in the core of the support, the support is mechanically stable. Because of mechanical action during use of the magnetizable aggregate the support therefore hardly suffers any wear, with the result that the magnetizable aggregate formed from the magnetizable support and the active component immobilized thereon can be separated repeatedly from the substrate or product mixture and used again without substantial loss in activity having to be accepted. According to an embodiment, the core of the support comprises at least 50% of the total volume of the support. Details regarding the support are explained further below.

According to the invention, therefore, a method for treating an organic and/or inorganic substrate is made available, wherein in a reaction chamber a substrate mixture is provided which contains the organic and/or inorganic substrate, a magnetizable aggregate is added to the substrate mixture, wherein the magnetizable aggregate comprises a magnetizable support and an active component immobilized on the magnetizable support;

the substrate mixture is converted to a product mixture with the magnetizable aggregate, and the magnetizable aggregate is separated from the product mixture with a magnetic separation device, wherein according to the invention the magnetizable support is present in the form of a particulate magnetizable support, wherein the particulate magnetizable support is constructed from a solid foam with a continuous phase which surrounds pores of the solid foam, wherein magnetizable areas which form a discontinuous phase are arranged in the continuous phase, and wherein the solid foam is closed-pore at least in the core of the particulate magnetizable support.

The method according to the invention can in principle be carried out with customary reactors which have a reaction chamber. The reactor can be operated batch-wise or also continuously. By a batch-wise operation is meant that the reaction chamber is filled with a specific quantity of substrate, the substrate mixture is converted to a product mixture, the product mixture is optionally removed from the reaction chamber and the product mixture is worked up. The substrate can be introduced in its entirety at the start of the conversion. However it is also possible to introduce only a part-quantity of the substrate at the start of the conversion and to feed further part-quantities of substrate into the reactor at time intervals ("fed-batch"). The concentration of substrate and product changes over time as the fermentation proceeds. If microorganisms or cells are used as active component, their concentration likewise changes as a result of their multiplication during the reaction.

With a continuous process, a near-constant concentration of the substrate, of the product as well as of the magnetizable aggregate is established in the reaction chamber. The organic substrate is fed to the reaction chamber, optionally after a start-up phase of the reactor, continuously, i.e. in a continuous feed, or semi-continuously, i.e. in several small portions, and a corresponding quantity of product is discharged from the reaction chamber. Thus a stationary equilibrium is established at which the concentration of substrate, product and magnetizable aggregate fluctuates only within narrow limits. The continuous or semi-continuous mode of operation is preferred in the method according to the invention.

The method of operating the reactor is not in principle subject to any limitations. It is for example possible to use a tank-shaped reactor, for example an agitated tank reactor in which the reactor content is moved continuously or in phases in order to homogenize the reactor content. The intensity with which the reactor content is moved depends on the specific form of the conversion which is carried out with the method according to the invention. If microorganisms or living cells are used as active component of the magnetizable aggregate the reactor content is preferably moved as gently as possible in order to prevent a biofilm immobilized on the magnetizable support being detached by shearing forces. It can be adequate for the reactor content to be moved for example only briefly once a day.

However, it is also possible to use a tubular reactor type, for example a tube reactor in which the substrate is passed through the reaction chamber in a plug-shaped or turbulent stream.

The reactor can be provided with customary equipment. For example it can be provided that the reactor can be thermostatted, thus a cooling or a heating is provided. Inlets and outlets with which a substrate can be fed or a product removed can be provided on the reactor. A stirrer with which the reactor content can be moved and mixed can be provided. Furthermore, devices can be provided for measuring temperature, pressure or various other process parameters such as for example pH. There are no limits per se to the design of the bioreactor or of the reaction chamber arranged therein. In particular for reactions which take place under anaerobic conditions, for example in the production of biogas, the reaction chamber is preferably designed closed.

A substrate mixture which contains the substrate is provided in the reaction chamber. The substrate mixture can be a solution. However, it is also possible for the substrate mixture to be designed as suspension, wherein also larger solid constituents, for example plant residues, can be contained in the substrate mixture. The substrate mixture contains preferably water as liquid phase. The substrate mixture can contain customary components, for example buffer systems, trace elements, cofactors or salts. The concentration of the individual constituents of the substrate mixture is chosen depending on the reaction carried out within customary ranges.

If the substrate mixture contains solids, the proportion of solids according to an embodiment is set at less than 50 wt.-%, according to a further embodiment less than 30 wt.-% and according to a further embodiment less than 5 wt.-%, calculated as dry weight of the solid constituents and relative to the weight of the substrate mixture. According to an embodiment, the solids content of the suspension is chosen such that the viscosity of the suspension is preferably so low that an efficient separation of the magnetizable aggregate is possible. If for example distillers grains are used as substrate the solids content is preferably chosen to be less than 3 wt.-% due to the high viscosity.

According to an embodiment, the solids content of the suspension is more than 0.1 wt.-%, according to a further embodiment more than 1 wt.-% and according to yet another embodiment more than 1.5 wt.-%.

The pH of the substrate mixture can be set depending on the reaction carried out. If, according to an embodiment, microorganisms are used for a fermentation, the pH is preferably chosen in the neutral range, preferably in the range of from 1 to 10, according to a further embodiment in the range of from 4 to 9 and according to a particularly preferred embodiment in the range of from 6 to 8. If enzymes are chosen as biocatalysts the pH of the substrate mixture is set according to their activity profile. The concentration of salts, trace elements or buffers is likewise chosen within usual ranges. The same applies for an embodiment in which capture molecules are used as active component.

The substrate mixture contains at least one organic and/or inorganic substrate which is converted with the magnetizable aggregate to a product mixture. As substrate there can be used, according to an embodiment, a substrate which is converted by the magnetizable aggregate to a product by means of a fermentation. In this embodiment the active component is formed preferably by a cell or a microorganism. In this embodiment organic and/or inorganic substrate and product thus have a different structure. In principle, any substrate which can be fermented can be chosen. Suitable organic substrates are for example sugars, such as for example glucose, or carbohydrates such as starch or celluloses, fats, fatty acids, glycerol, nitrogen-containing substrates such as proteins, protein hydrolyzates, peptides, amino acids or amino-acid mixtures. However, depending on the fermentation carried out, complex mixtures such as for example organic waste such as liquid manure, slurry, manure, plant chaff, silage, out-of-date seeds or even waste water or sewage sludge, as well as digestates, distillery residues, whey, algae suspensions, industrial organic residues, cooking residues, food past its use-by date, flotation fats etc. can also be used as organic substrate.

However, the organic and/or inorganic substrate can also be a molecule, preferably biologically active, which is separated off from a substrate mixture, for example a culture medium, with the help of the method according to the invention. The substrate molecule is bonded to the magnetizable particulate support via a capture molecule without a chemical reaction occurring. In this embodiment of the method, the structure of the organic substrate remains unchanged during transformation to a product mixture. pH, salt concentration and other parameters are suitably chosen such that a strong bond between organic substrate and magnetizable aggregate or capture molecule is achieved.

The active component is immobilized on a special magnetizable support. The immobilization can be achieved with customary methods. For example an enzyme or an enzyme complex or a capture molecule can be adsorbed on the surface of the support or also be covalently bonded to the surface of the support with the help of a spacer. Where microorganisms are used as active component, according to a preferred embodiment these settle on the surface of the magnetizable support and there form colonies or a biofilm. According to another embodiment the microorganisms can also be fixed artificially with the help of polymers biologically degradable to a greater or lesser extent such as e.g. polycaprolactone or poly-3-hydroxybuturate or e.g. alginate or the like on the surface of the magnetizable support by enclosing them in the polymer matrix. The surface of the magnetizable support can also have been previously chemically modified/coated in order to facilitate the attachment of enzymes, microorganisms or capture molecules. If microorganisms or cells are used as active component of the magnetizable aggregate, the magnetizable support can for example be coated with a nutrient solution, trace elements or also compounds which facilitate a growth of microorganisms or cells on the magnetizable support. Various components can also be contained in the coating. An example of a coating is a coating with xanthan which is combined with trace elements or a combination of nutrients. Customary compounds as are known from microbiology are used as trace elements or nutrients.

In the discontinuous, thus batch-wise, mode, the magnetizable aggregate is preferably already added to the substrate mixture at the start of the conversion. If supported enzymes are used as biocatalytically active system, suitably the whole quantity of enzymes is provided in supported form. The same applies if capture molecules are used as active component. When using microorganisms as active component also only a part of the required microorganisms can be added to the substrate mixture in supported form. In this embodiment, the substrate mixture is thus seeded with the microorganisms, wherein the microorganisms can also already be present in supported form. During the fermentation the microorganisms can multiply and optionally also colonize fresh magnetizable support which is added to the substrate mixture. Then, in customary manner, a conversion to a product mixture takes place which is then worked up optionally after prior removal from the reaction chamber.

With a continuous mode, which is preferred in particular when using microorganisms, the operating state of the reactor must first be reached, thus a stationary equilibrium established in the reaction chamber.

According to a first embodiment, with the method according to the invention an organic and/or inorganic substrate is continuously removed from a substrate or product mixture. The removal can take place in a continuous stream or also portion-wise. A continuous removal makes possible a continuous procedure in the reaction chamber of a reactor, i.e. a dynamic equilibrium in which substrate is fed to the reaction chamber and product is removed from the reaction chamber, wherein the conditions in the reaction chamber remain substantially unchanged, can be established in the reaction chamber.

The substrate mixture can for example be a culture medium in which a specific active ingredient is produced with the help of a microorganism using biotechnology. The active ingredient can be the organic substrate itself which is removed from the culture medium with the method according to the invention. However, the organic substrate can also belong to another group of substances, e.g. substances which have an inhibiting effect on the biotechnological process (inhibitors).

According to this embodiment, a component which has for example an inhibiting effect on the reaction occurring in the culture medium, for example because it has an inhibiting effect on the growth of cells, can thus be continuously removed from the culture medium.

A capture molecule would be used as supported active component in this embodiment. The capture molecule would then be able to bind the organic and/or inorganic substrate with the result that the latter could be removed from the substrate mixture via a magnetic separation device with the help of the magnetizable aggregate. Microorganisms can be contained in the culture medium in this embodiment, but substantially not bonded to the magnetizable support.

Microorganisms and magnetizable aggregate can be contained together in the culture medium. However, an embodiment in which in a first step the microorganisms are separated off from the culture medium and in a further step the organic substrate is separated off from the remaining medium with the help of the magnetizable aggregate is also possible.

Removing an organic and/or inorganic substrate from a substrate mixture was described with reference to the isolation of an organic substrate from a culture medium, wherein the organic substrate was produced in a biotechnological process with the help of microorganisms. However, the substrate can also have been produced in other ways. In principle, there are no limitations here. The organic and/or inorganic substrate can in principle also have been produced in a chemical reaction. The substrate is bonded via the capture molecule to the magnetizable aggregate by non-covalent bonds, which is then separated off from the substrate or product mixture by means of a magnetic separator.

According to a further preferred embodiment, the magnetizable aggregate is formed from a magnetizable support and a microorganism immobilized thereon. The conversion of the substrate is effected by the microorganism. In this embodiment, the magnetizable aggregate is preferably discharged from the bioreactor with the product mixture and fed to a magnetic separation device. In the magnetic separation device the magnetizable aggregate is then separated off from the product mixture and can optionally be returned to the reactor.

Generally, in the method according to the invention, the reaction chamber is filled with the substrate mixture and the organic and/or inorganic substrate converted with the magnetizable aggregate to a product mixture until a reaction equilibrium has been established. The equilibrium can be stationary or also a dynamic equilibrium. Further reaction components, for example nutrients, can optionally be added during the conversion.

At the start of the reaction, thus when the reactor is charged for the first time or afresh with organic and/or inorganic substrate, the magnetizable aggregate can already be added to the substrate mixture. This is preferred for example in enzymatic fermentations in which the supported enzyme is already added to the substrate mixture at the start of the fermentation. This embodiment is also preferred if an organic substrate is to be separated off from a product mixture with the method according to the invention, thus the magnetizable aggregate comprises a magnetizable support as well as a capture molecule immobilized thereon. If microorganisms are used as biocatalysts, these can be added in a form in which the relevant microorganisms have already colonized the support or have also been artificially immobilized on the support. This can take place for example by immobilization of the microorganisms by enclosure. The microorganisms are enclosed in a layer of polymer which is deposited on the surface of the magnetic support. According to an embodiment, a polymer is used for the immobilization of the microorganisms.

According to another embodiment, a mixture of at least two polymers is used for the immobilization of the microorganisms. One of the polymers can easily be decomposed by the microorganisms. In the colonization phase this polymer also serves as nutrient for the microorganisms. Its proportion in the polymer mixture is chosen preferably in the range of from 10 to 40 wt.-%, relative to the total weight of the polymer mixture. A suitable polymer is for example poly-3-hydroxy-butyrate. The second polymer is scarcely biodegradable. It serves above all as framework substance. Its proportion is preferably chosen to be in the range of from 60 to 90 wt.-% relative to the total weight of the polymer mixture. A suitable scarcely biodegradable polymer is for example polycaprolactone.

However, according to another embodiment, the procedure is that the magnetizable support is added to the substrate mixture without a prior colonization by microorganisms and the substrate mixture is seeded with the relevant microorganism or with a relevant mixture of microorganisms. For this, microorganisms for example in the form of liquid or solid seeding material from other fermentation units can be added in the start-up phase.

During a start-up phase the microorganisms multiply, wherein also the magnetizable support added to the substrate mixture is colonized by the microorganisms, with the result that according to the invention a magnetizable aggregate forms. Optionally during the start-up phase, fresh organic substrate can be added and spent substrate or optionally already product mixture removed from the reaction chamber. During the start-up phase suitable process parameters such as pH, temperature, substrate concentration, intermediate concentration, end-product concentration or degree of colonization of the magnetizable support by microorganisms are regularly monitored, in order to monitor the stability of the fermentation. If a sufficient quantity of microorganisms is available and a stationary equilibrium has been established in the reaction chamber, the operating state of the bioreactor has been reached. In a continuous mode of operation fresh organic substrate is added and spent substrate, i.e. product mixture, discharged from the reaction chamber continuously or at time intervals.

Once the operational state has been established in the continuous mode of operation of the reactor, the substrate mixture on the supported biocatalytically active system, in particular the at least one microorganism, is continuously converted to a product mixture. For this, fresh substrate mixture is continuously fed to the reaction chamber and a corresponding quantity of product mixture removed from the reaction chamber. The product mixture can then be further processed.

The product mixture can contain solid, liquid or also gaseous components. A product mixture can for example be a solution or suspension in which the product has accumulated.

However, according to an embodiment, the product mixture can also consist of a solution or suspension as well as a gaseous component. The gaseous component is collected and regularly discharged from the reaction chamber. The liquid and solid components can be discharged from the reaction chamber optionally separately via a separate outlet. In this embodiment the liquid or solid component can form a digestate for example during biogas production, while the gaseous component, for example a methane-containing gas, is obtained as further product component.

During working up of the product mixture the magnetizable aggregate according to the invention is separated from the product mixture with a magnetic separation device. All magnetic separation devices known per se can be used as magnetic separation device. For example permanent magnets which can be arranged stationary or movable in or at the separation device are suitable. However, similarly, for example electromagnets can also be used. Stationary magnets collect the magnetizable aggregate at a specific location in the separation device, while movably arranged magnetic separation devices can transport the magnetizable aggregate after separation, for example to a specific location, and collect it there. For this, for example a permanent magnet can be displaced along an outer wall of a separation tube. Once the magnetizable aggregate has been separated from the product mixture with the help of the magnetic separation device, it can be collected for example by switching off the magnetic separation device with the result that the magnetizable aggregate for example is detached again from a wall of the magnetic separation device and for example can be rinsed and collected.

The magnetic separation device can be arranged in the reaction chamber itself, for example as an encased rod-shaped magnet. However, it is also possible to provide the separation device outside the reaction chamber and to transfer the product mixture, for example a digestate, from the reaction chamber into the magnetic separation device. The magnetic separation device is preferably located in the outlet of the reactor.

Experience shows that, when passing through the magnetic separator, not all magnetizable aggregates are removed from the product mixture, with the result that losses must be accepted. In particular when starting up the process magnetizable aggregates that are only weakly magnetizable are not separated from the product mixture by the magnetic separator. This can for example be because the particles of the magnetizable support are too small, with the result that, at a given viscosity of the product mixture and a given product flow through the magnetic separator, they are not detected by the magnetic separator. During start-up of the conversion therefore a selection can take place within the magnetizable supports or aggregates with the result that the size distribution of the supports changes compared with the original state.

In the method according to the invention a special support is used on which the active component is immobilized in order to form, according to the invention, a magnetizable aggregate. By using a particulate support the magnetizable aggregate can be distributed homogeneously in the substrate mixture. This makes possible an efficient execution of the method, as for example a fermentation of the organic substrate can take place uniformly in the whole reaction chamber.

The particulate support is made of a solid foam. The solid foam lends the support a high mechanical stability with the result that it can also withstand higher mechanical loads as for example occur if the method according to the invention is used for producing biogas. At least in the core of the support the solid foam has a closed-pore structure. The closed pores, which are filled with gas, lend buoyancy to the magnetizable support if it is introduced into a liquid, in particular aqueous, medium.

Because of the core made of a closed-pore foam, the particulate support can be designed relatively large without the magnetizable support having a high specific weight and thus a high sedimentation rate. According to an embodiment, the magnetizable support has a diameter of up to 10 mm, according to a further embodiment a diameter of up to 5 mm, according to a further embodiment a diameter of up to 2 mm.

The size of the magnetizable support can be set with customary methods, for example screening or air separation. In order to be able to manipulate the magnetizable support well and in particular separate it again from the process mixture within technically useful processing times, it has proved advantageous if the diameter of the support is chosen to be greater than 50 µm, according to a further embodiment greater than 100 µm. In particular if microorganisms are used as biologically active component the diameter of the magnetizable support is preferably chosen to be at least so large that the microorganisms can grow on the support. According to an embodiment, the diameter of the magnetizable support is at least 150 µm, according to a further embodiment at least 200 µm. The size of the magnetizable support can be determined for example by screening.

If the method according to the invention is used to isolate an organic and/or inorganic substrate from a substrate mixture by adsorption using the magnetizable aggregate, it is preferred that the magnetizable support has a relatively small diameter as thereby a high surface area is produced on which the active component is provided in the form of a capture molecule which in turn can enter into a non-covalent bond with the substrate in order to bond the substrate to the magnetizable aggregate. In this embodiment, the average diameter $D_{50}$ of the magnetizable support is preferably chosen smaller than 500 µm, according to a further embodiment smaller than 300 µm. In order to achieve an efficient separation of the magnetizable aggregate from the substrate or product mixture the diameter of the magnetizable support is preferably chosen greater than 0.5 µm, according to an embodiment greater than 1 µm. According to an embodiment, the diameter of the support is less than 2 mm, according to another embodiment less than 1 mm.

The particulate support can have a spherical shape. However, it is also possible to give the support a different geometric shape, for example that of an irregularly shaped three-dimensional body.

The support has closed pores in the solid foam, at least in its core. The density of the support can be set, in particular lowered, by the proportion of closed pores in the total volume of the magnetizable support. Therefore it is not necessary, as with the methods known from the state of the art, to choose the dimensions of the magnetizable particles to be small in order to stop or at least slow down a sedimentation of the support. Due to the closed pores, the density of the support during its use in the fermentation can at most slightly increase by the entry of water. The density of the magnetizable support is preferably chosen in the range of from 0.8 to 1.2 g/ml. The particle bulk density of the magnetizable support can be determined according to DIN V18004, 5.3 (EN1097-6:2000).

The size of the pores can in principle be chosen as desired. Preferably the pore size is chosen such that the support with the biocatalyst immobilized thereon displays no substantial inclination towards sedimentation or flotation in the substrate mixture and the mechanical stability of the support is ensured.

The support can have a closed-pore foam structure over the whole of its volume. In this case the magnetizable support has on its outer surface a relatively smooth structure with a substantially continuous skin. However, according to another embodiment the magnetizable support has a closed-pore structure only in its core or only in one part of its volume. Thus inside the magnetizable support the core forms a section in which the solid foam has a closed-pore structure.

As a result of the foam structure, in spite of its low weight the magnetizable support has a high mechanical stability. The support also withstands mechanical stresses which for example act on the support by shearing forces when the substrate mixture is moved or during magnetic separation. The support can therefore be used over a long period of time in the process without substantial wear occurring. In order to maintain a continuous process with the magnetizable aggregate being returned to the reaction chamber it is sufficient to supplement only the proportion of the support or of the magnetizable aggregate in the substrate mixture which is unavoidably lost due to the incomplete magnetic separation.

The solid foam of the support comprises a continuous phase. The continuous phase is preferably formed from a network former. All compounds which can form a continuous structure can be used as network formers. Such molecules are for example organic or inorganic polymers. Examples of organic polymers are polystyrene, polyurethane, polyethylene, polypropylene and polyoxymethylene. The list is to be viewed only as an example and not as exclusive. Examples of inorganic network formers are glasses. The network former is stable under the conditions under which the fermentation is carried out. Preferably it displays no solubility in the liquid phase, in particular water, which is contained in the substrate mixture. Magnetizable areas which according to an embodiment form a discontinuous phase are arranged in the continuous phase. The magnetizable areas can for example be formed by magnetizable particles which are arranged in the continuous phase. The magnetizable areas are preferably surrounded by the continuous phase with the result that the magnetizable areas are arranged within the continuous phase. The magnetizable areas can thereby be prevented from being affected by corrosion processes and for example dissolved out. The support is preferably not intended to interact with the substrate mixture or the active component, which has a negative effect on the method, for example if the method is used for a fermentation and the active component is formed by a microorganism or an enzyme.

The magnetizable areas or the magnetizable particles are preferably homogeneously distributed in the continuous phase of the network former. The extent of the magnetizable areas is preferably chosen to be small. According to an embodiment, the magnetizable areas have a diameter of less than 500 µm. According to an embodiment, the diameter of the magnetizable areas lies in the range of from 100 nm to 400 µm, according to a further embodiment in the range of from 200 nm to 100 µm. In practical application it has proven advantageous if the size of the magnetic particles is chosen in a range of from 0.3 to 25 µm.

The magnetizable areas can also be formed by nanoparticles which preferably have superparamagnetic properties. According to an embodiment, the diameter of the magnetizable areas lies within a range of from 1 nm to 500 µm, preferably 1 nm to 100 µm. In order to have superparamagnetic properties the size of the magnetizable particles is preferably chosen in a range of from 1 to 10 nm. The particle size of the magnetizable areas can be suitably determined after the grinding of the starting materials. After being fused into the network former, in particular glass, the diameter of the magnetizable particles can be determined only with great difficulty.

Large quantities of magnetizable particles can be provided in the support by the homogeneous distribution of the magnetizable areas in the particulate support. Therefore, at a predetermined field strength, a greater force can be applied to the particulate support in the magnetic separator, with the result that the supported biocatalyst or generally the magnetizable aggregate can be separated off more rapidly and thus more completely from the product mixture.

The proportion of the magnetizable particles through which magnetizable areas can be formed in the continuous phase of the solid foam is preferably chosen in a range of from 8 to 40 wt.-%, according to a further embodiment in the range of from 15 to 30 wt.-% and according to a further embodiment in the range of from 18 to 25 wt.-%, relative to the weight of the support. The proportion of the continuous phase, preferably of the network former, in particular the glass phase, is preferably chosen in the range of from 92 to 60 wt.-%, according to a further embodiment in the range of from 85 to 70 wt.-% and according to a further embodiment in the range of from 82 to 75 wt.-%. The percentage proportions relate to the weight of the particulate support and correspond substantially to the proportions of magnetizable particles and to the material of the continuous phase as used in the production of the support.

The quantity of the magnetizable aggregate provided in the substrate mixture is chosen depending on the conditions under which the method according to the invention is carried out. Relative to the weight of the dry organic substrate the quantity of the magnetizable aggregate according to an embodiment is chosen in the range of from 1 to 70 wt.-%, according to a further embodiment in the range of from 1 to 20 wt.-% and according to yet another embodiment in the range of from 2 to 5 wt.-%.

As already explained, the separation of the magnetizable aggregate from the product mixture can already take place in the reaction chamber. This method can be applied for example in the discontinuous method, for example in batch-wise fermentations. For this, for example a magnetic separation device, for example an encased rod-shaped magnet, can be dipped into the product mixture. Once the magnetizable aggregate has collected on the magnetic separation device the separation device with the adhering magnetizable aggregate is removed from the product mixture again.

However, according to a preferred embodiment it is provided that the product mixture is transferred from the reaction chamber into a magnetic separation device in which the magnetizable aggregate is then separated off from the product mixture. Such an embodiment is advantageous in particular if the method is carried out in a continuous mode of operation. A specific quantity of the product mixture is discharged from the reaction chamber and fed to the magnetic separation device. The discharge can take place in portions or in a constant product stream. For example a tube through which the product mixture is passed can be provided as magnetic separation device. For example a rod-shaped magnet on which the magnetizable aggregate accumulates can be provided inside the tube. However, it is also possible to arrange magnets on the outer wall of the tube with the result that the magnetizable aggregate precipitates on the inner wall of the magnetic separation device. The shape of the magnetic separation device as well as the strength of the magnets used is chosen such that as high as possible a separation rate of the magnetizable aggregate is achieved. According to an embodiment, more than 60 wt.-%, according to a further embodiment more than 80 wt.-% and according to yet another embodiment more than 90 wt.-% and according to yet another embodiment more than 98% of the magnetizable aggregate contained in the product mixture is separated off in the magnetic separation device. The percentages refer to a single pass of the substrate through the magnetic separation device. A complete separation of the magnetizable aggregate or of the supported biocatalyst is difficult to achieve when carrying out the method on an industrial scale. After passing through the magnetic separation device, preferably less than 1 wt.-%, according to a further embodiment less than 0.5 wt.-% and according to yet another embodiment less than 0.1 wt.-% of the magnetizable aggregate originally contained in the product mixture after discharge remains in the product mixture.

The magnetizable aggregate separated off from the product mixture can be recovered and optionally used in another method, for example a further fermentation.

According to a preferred embodiment, the magnetizable aggregate separated off from the product mixture is returned to the reaction chamber. In this way, in particular with continuous fermentations, the stationary quantity of biocatalytically active system, in particular microorganisms, can be increased in the reaction chamber of the reactor. The reactor load, i.e. the throughput of organic substrate, and thus the yield of product, can thereby also be increased. This is advantageous in particular if very slow-growing microorganisms are used as active component of the magnetizable aggregate.

According to an embodiment, the microorganisms used as biologically active component have a generation time of more than 8 hours, according to a further embodiment more than 24 hours. By generation time is meant the period within which the cells divide once under optimum growth conditions, i.e. within which the number of cells doubles. The generation times depend greatly on the reaction conditions and can multiply under unfavourable conditions. Fast-growing microorganisms such as e.g. $E.\ coli$ have a generation time of only 20 mins under optimum growing conditions. Slow-growing microorganisms, e.g. some nitrifying agents, have generation times of 8-24 h under optimum growing conditions. Under non-optimum conditions, e.g. at wintry temperatures in wastewater purification plants, their generation times can increase to >18 d. Very slow-growing microorganisms such as most methane gas bacteria or the so-called anammox bacteria can have even longer generation times. Thus e.g. the methane gas bacterium *Methanosaeta* sp. has generation times of 1-3 d even under optimum growing conditions. Under sub-optimum conditions these generation times can increase to 20 days or even longer.

All available methods can be used to return the separated magnetizable aggregate to the reaction chamber. The return can be carried out continuously or portionwise by, for example, firstly collecting a specific quantity of magnetizable aggregate and then returning this to the reaction chamber. The return can be automated. However, it is also possible to carry out the return manually. The advantages of the method according to the invention are evident in particular in fermentations with slow-growing microorganisms.

According to a preferred embodiment, microorganisms are used as active component of the magnetizable aggregate. The microorganisms are preferably provided in the form of a biofilm on the magnetizable support. A biofilm forms on the support during the start-up phase of the reactor. When starting up the reactor, firstly a colonization of the magnetizable support takes place through microorganisms which, by further growth, then form individual colonies which can then merge as the process continues and can form a continuous biofilm on the support. Due to the high density of microorganisms, biofilms, in particular if they are arranged on particulate supports, are very efficient biocatalysts for fermentations.

In the method according to the invention, a special magnetizable support is used, at least the core of which is constructed of a closed-pore solid foam. As already explained, in principle all materials capable of forming a continuous, preferably glass-type network structure, can be used as continuous phase of the solid foam. Due to their high mechanical stability and the usual ease of availability of the raw materials, it is preferred if the continuous phase of the particulate support is formed from an inorganic material. It is, in turn, particularly preferred here if the inorganic material is a glass, in particular a silicate glass.

Glasses are available in different compositions and qualities. However, because for example in fermentations there are usually no aggressive reaction conditions, suitable glasses which for example have a high content of alkali metal, in particular sodium, can be used. Such glasses are also called soda glasses and are used for example to produce glass containers and plate glass. According to an embodiment, in particular the support can comprise a continuous glass phase which is produced from recycled glass. Other constituents which for example are introduced via the recycled glass can thereby also be contained in the glass in addition to the customary constituents such as $SiO_2$, $Na_2O$, $K_2O$, $CaO$. Examples of components are $B_2O_3$, $Al_2O_3$ or iron and manganese oxides. These further constituents are preferably contained in the continuous phase in a proportion of less than 10 wt.-%, according to a further embodiment in a proportion of less than 8 wt.-%, relative to the glass phase.

In the method according to the invention, the magnetizable aggregate is separated off from the product mixture by means of a magnetic separation device. In order to make the procedure suitable for commercial processes the separation should be able to take place within a suitably short period of time. For this, the magnetic separation device should be able to exert a sufficiently high force on the support that the latter can be transported at a sufficiently high speed in the product mixture to the desired location.

According to an embodiment, it is provided that the particulate support has a magnetic mass susceptibility in the range of from $5 \times 10^{-9}$ to $3.7 \times 10^{-7}$ m$^3$/kg.

In order to avoid an agglomeration of the magnetizable aggregate without the influence of an external magnetic field, materials which, after switching off an external magnetic field, display only a low residual magnetism are preferably used for the magnetizable areas. The residual magnetism can be read from the so-called magnetization curve. A material is exposed to an external magnetic field and is itself magnetized to a greater or lesser extent. By reducing the field strength, starting from the magnetic saturation, to the value of zero, a residual magnetization remains. This is measured in millitesla (mT). The residual magnetism then completely disappears if a magnetic force which is oppositely poled to the original field is applied to the material with the field strength Hc (coercive field strength).

According to a first embodiment, the magnetizable areas in the particulate magnetizable support are formed by a superparamagnetic substance. After switching off an external magnetic field, a superparamagnetic substance no longer displays any residual magnetism. A suitable superparamagnetic substance is for example magnetite in the form of nanoparticles.

According to a further embodiment, the magnetizable areas are formed by a ferrimagnetic material. After switching off an external magnetic field, ferrimagnetic materials display only a low residual magnetism. Suitable ferrimagnetic materials are for example ferrite, ferrites and maghemite.

The method according to the invention shows its advantages in particular if slow-growing microorganisms are used as active component of the magnetizable aggregate. For thermodynamic reasons, anaerobic microorganisms display only a relatively slow growth. According to an embodiment, the active component of the magnetizable aggregate is therefore formed by a pure culture of a species of microorganism, by a defined mixed culture of several species of microorganism, or by a mixed biocoenosis of anaerobically growing microorganisms. According to an embodiment, it is then provided that the conversion of the substrate mixture on the magnetizable aggregate, which comprises as active component anaerobically growing microorganisms, to a product mixture is carried out under anaerobic conditions.

Particularly good results, i.e. a high yield of product as well as a high substrate throughput, is achieved if the separated-off magnetizable aggregate, wherein the active component is formed by at least one anaerobically growing microorganism, is returned to the reaction chamber as in this way with anaerobic microorganisms the stationary concentration can be markedly increased.

According to a preferred embodiment the microorganisms are methanogenic bacteria. Examples of methanogenic bacteria are *Methanosaeta concilii, Methanosarcina barkeri, Methanosphaera stadtmanae, Methanobrevibacter ruminantium, Methanobacterium formicicum, Methanococcus voltae*, as well as *Methanoculleus palmolei*. The list is not to be viewed as exclusive.

Methanogenic bacteria are used for example for producing biogas. According to a particularly preferred embodiment, the method according to the invention is therefore formed as a method for the production of biogas.

If the method according to the invention is used to produce biogas, reactors known per se can be used to produce biogas, wherein these reactors are provided with a magnetic separation device with which the microorganisms immobilized on the magnetizable support can be removed from the digestate. A suitable fermenter is described for example in DE 10 2005 024 886 B3 or US2009/0305377.

Customary materials, for example biowaste, green waste, commercial waste, food waste, agricultural waste, kitchen waste, organic waste or renewable raw materials and similar materials can be used as organic substrate.

The substrate mixture can have a high water content. According to an embodiment, the water content of the substrate mixture is chosen in the range of from 50 to 99 wt.-%, according to a further embodiment in the range of from 60 to 95 wt.-%.

The residence time of the organic substrate in the reaction chamber depends on the type of organic substrate used and the reaction conditions in the fermenter and can be between a few hours, for example 2 hours, and several days, for example up to 40 days, and in some cases also up to several months, for example up to three months.

If the method is developed for example as a method for producing biogas, according to an embodiment the residence time of the organic substrate in the reaction chamber can be chosen in the range of from 3 to 28 days.

The throughput of organic substrate in the reaction chamber is set, according to an embodiment, in the range of from 1 to 10 kg organic dry substance/$m^3$ day. The throughput of organic substrate is limited in principle only by the conditions specific to the plant, with the result that higher throughputs are also possible.

The method can be carried out in a single reactor. However, it is also possible to connect several reactors in series and to operate the method in several stages. The different stages of the method can then be optimized to specific parameters. Thus in biogas production an embodiment is possible in which the organic substrate is broken down in a first reaction stage and the broken-down organic substrate is then fermented in a second stage, wherein biogas is produced.

The fermentation gas produced during biogas production contains substantially carbon dioxide, methane, hydrogen and hydrogen sulphide. Oxygen, if it enters the reaction chamber, is rapidly consumed.

If the method according to the invention is designed as a fermentation method for producing biogas, the process temperature in the reaction chamber is chosen, according to an embodiment, between 30 and 70° C., according to a further embodiment in the range of from 35 to 42° C. or 50 to 65° C. Mesophilic or thermophilic methanogenic bacteria have their preferred range in these ranges.

The pH in the reaction chamber can be between 3.5 and 8.5 locally. In order to achieve a high rate of methane formation, it is advantageous to set a neutral pH in the reaction chamber during biogas production. The pH of the substrate mixture in the reaction chamber is preferably set in the range of from 6.5 to 8.0.

The C/N-ratio of the organic substrate used in biogas production is chosen, according to an embodiment, greater than 20:1, according to an embodiment greater than 30:1 and according to a further embodiment greater than 40:1.

The organic substrate can be introduced into the reaction chamber using customary devices. For example, the organic substrate can be introduced into the reaction chamber using a liquid-tight conveyer. The organic substrate can, for example, be introduced into the reaction chamber through a channel from a substrate reservoir using a liquid-tight conveying screw. However, the organic substrate can also be fed in using non-liquid-tight conveying apparatus.

In order to be able to separate the magnetizable aggregate as completely as possible from the product mixture which is formed by a digestate in the case of biogas production, it is preferred that the product mixture has a high water content. This makes possible a sufficient mobility of the magnetizable aggregate in the product mixture and thus a rapid separation. The product mixture preferably has a water content of more than 50 wt.-%, according to an embodiment a water content in the range of from 70 to 99 wt.-%. The product mixture discharged from the reaction chamber can optionally be diluted with water.

The product mixture can be discharged from the reaction chamber using customary methods and devices. A suitable device is, for example, a liquid-tight conveying screw. After separation of the magnetizable aggregate, the remaining product mixture can be pressed off and the liquid phase completely or partially returned to the reaction chamber again. The stationary concentration of microorganisms can thereby be further increased.

The fermentation gases which form during biogas production can be drawn off at the head of the reaction chamber. The biogas can then be processed in customary manner, for example by separating off sulphurous compounds.

In order to facilitate the breaking down of the organic substrate, enzymes, for example, can be added to the substrate mixture. Examples of enzymes are cellulases, hemicellulases, lipases, proteases and/or amylases.

During biogas production, preferably low-cost materials are used. Chalk- or ammonium-based buffers, for example, can be used as oxygen buffers.

Nickel, cobalt, molybdenum, selenium and/or tungsten can be added to the substrate mixture as trace elements. Methane bacteria in particular have a high requirement for trace elements.

The magnetizable aggregate used in the method according to the invention can be used in various applications. It can, as described above, be used to immobilize a biocatalytically active system, for example an enzyme or a microorganism, such as e.g. a monoculture, a defined mixed culture or a mixed biocoenosis of species of bacteria, species of fungi or cell culture cells. However, the magnetizable aggregate can also be used, for example, to separate off specific substances from a mixture in that the compound concerned is adsorbed by the active component on the magnetizable aggregate. This can be a direct adsorption or an indirect bond. The magnetizable particulate support can have been coated in advance, e.g. with the following substances as active component: streptavidin, avidin, protein A, immunoglobulins (IgGs) or the particle surface can have been modified previously with —$NH_2$ or —COOH groups. Likewise, gene probes or other capture molecules can be attached to the particle surface.

The subject of the invention is therefore also a magnetizable aggregate, comprising a particulate magnetizable support made of a solid foam with a continuous phase, which is preferably constructed from a network former and which surrounds pores of the solid foam, wherein magnetizable areas are arranged in the continuous phase, wherein the foam is closed-pore at least in the core of the magnetizable support, and wherein also at least one active component is immobilized on the surface of the particulate magnetizable support.

The properties and the structure of the particulate magnetizable support have already been described above in part in the description of the method.

The particulate magnetizable support consists of a solid foam in which the pores of the solid foam are surrounded by a continuous phase. The continuous phase is preferably formed from a network former. The network former is preferably provided by a glass, in particular a silicate glass. For example, quartz glass, boron glass or also a glass containing aluminium oxide can be used as a glass. However, in particular for use in biotechnology systems, for example the above-described fermentation, relatively low-cost glasses can be used, for example soda glass or ground recycled glass. The glasses preferably contain silicon dioxide as their main constituent. An example of a glass has a composition of 68.5 to 75 wt.-% $SiO_2$, 10 to 14 wt.-% $Na_2O$, 6 to 11 wt.-% CaO. As a further constituent, it can contain for example $Al_2O_3$ in a proportion of 1.5 to 3 wt.-%, $K_2O$ in a proportion of up to 2.5 wt.-%, MgO in a proportion of 0.5 to 4 wt.-%, as well as BaO in a proportion of up to 3 wt.-%. Further constituents which can be introduced for example by the recycled glass as impurities are, according to an embodiment, contained in a proportion of less than 2 wt.-%, according to a further embodiment in a proportion of less than 1 wt.-%. Such impurities are, for example, iron oxide or titanium oxide. The proportion of the glass or of the continuous phase on the particulate magnetizable support is preferably chosen in the range of from 70 to 85 wt.-%. The proportion of the magnetizable particles from which the magnetizable areas of the particulate support are formed is preferably chosen in the range of from 15 to 30 wt.-%.

The magnetizable support has a core made of a closed-pore foam. The core preferably occupies at least half, according to a further embodiment at least two thirds, of the total volume of the magnetizable support. The core can be arranged centrally in the centre of the magnetizable support. However, it is also possible that the centre of the core is displaced relative to the centre of the magnetizable support.

According to an embodiment, the particulate support has a continuous skin on its surface, with the result that the pores arranged inside the particulate support are closed.

The particulate support preferably has a low water absorption capacity. The water absorption capacity of the particulate support, determined according to DIN EN 13055/DIN V 18004 5.3 and additionally EN1097-6:2000 is preferably 0 to 50 wt.-%, according to an embodiment less than 35 wt.-% and according to a further embodiment less than 10 wt.-%.

According to an embodiment, the particulate support according to the invention is present in the form of approximately spherical particles. Details of the diameter of the magnetizable support have already been given above. According to a further embodiment, the diameter of the support, measured as average particle size, is in the range of from 0.5 μm to 5 mm, according to an embodiment in the range of from 100 μm to 2 mm. By an average particle size is meant the volume-related particle size $D_{50}$, wherein 50% of the particles have a larger diameter than $D_{50}$ and 50% of the particles have a smaller diameter than $D_{50}$. The average particle size $D_{50}$ can be ascertained for example by screen analysis. Suitable methods are given for example in DIN 66165-1 and -2. Alternatively the average particle size can be measured by means of laser diffraction. Suitable methods are described in ISO 13320:2009.

At least sections of the particulate support preferably have an irregularly shaped surface. This makes it easier for microorganisms to grow on the surface of the particulate magnetizable support. Such an irregular surface can be produced, for example, by carefully grinding the particulate support after foaming, with the result that the foamed magnetizable support is broken. Broken-open pores are then obtained at the broken surfaces. With such an embodiment, at least sections of the surface of the particulate magnetizable support have sharp-edged ridges as well as depressions resulting from the broken-open pores. Such a structure can for example be established with the help of a reflected-light microscope or a scanning electron microscope.

The particulate magnetizable support contained in the magnetizable aggregate according to the invention preferably has a bulk density in the range of from 100 to 1000 kg/m$^3$, according to an embodiment a bulk density in the range of from 200 to 800 kg/m$^3$ and according to a further embodiment a bulk density from 300 to 600 kg/m$^3$. The bulk density can be ascertained according to DIN EN 13055-1.

According to a further preferred embodiment, the particulate support has a particle bulk density of less than 2000 kg/m$^3$, preferably a particle bulk density in the range of from 300 to 1500 kg/m$^3$ and according to a further embodiment a particle bulk density in the range of from 600 to 1000 kg/m$^3$ auf. The particle bulk density is the quotient of the mass of the dry particulate magnetizable support and the volume of the water-saturated particulate support. It is determined according to DIN EN 13055-1 and DIN V 18004, 5.2.

If the particle bulk density is set in this range, a sedimentation or floating of the particulate magnetizable support, which is optionally provided with a biofilm immobilized thereon, can advantageously be effectively suppressed.

According to an embodiment, the support according to the invention has a transformation temperature of less than 800° C., in particular a range of from 500 to 750° C. The transformation temperature is the temperature at which glass passes from the plastic range to the rigid state during cooling.

Small, preferably predominantly crystalline particles of a magnetizable material are enclosed in the continuous phase preferably formed from the network former, in particular glass phase, of the particulate magnetizable support. The magnetizable particles preferably have a diameter of less than 500 μm, according to an embodiment a diameter in the range 1 nm to 400 μm, according to a further embodiment a diameter in the range 10 nm to 100 μm. The magnetizable particles are preferably distributed homogeneously in the continuous phase of the solid foam.

According to a further embodiment very small particles of the magnetizable material are used. The use of very small particles with a diameter of less than 500 nm, according to an embodiment less than 100 nm, according to a further embodiment less than 10 nm, also makes it possible to produce for example superparamagnetic particles. According to an embodiment, nanoparticles are used to provide the magnetizable ranges. In this embodiment the particles for the magnetizable ranges preferably have a particle diameter in the range of from 1 nm to 10 nm.

The details on particle size relate to the average particle size diameter $D_{50}$. In principle, the width of the particle size distribution has no significant influence on the properties of the magnetizable support or magnetizable aggregate. The particle size distribution is preferably set so that the magnetizable particles are completely enclosed by the continuous phase of the magnetizable support.

In the case of larger particles (>100 μm) the particle size distribution can be ascertained for example by means of screen analysis. In the case of smaller particles the average particle diameter can be measured by laser diffractometry. In order to determine the particle diameter, it is assumed that the particle size of the magnetizable particles no longer changes during foaming of the granular material.

The particles of the magnetizable material are preferably completely enclosed in the continuous phase, with the result that corrosion of the magnetizable particles as well as interactions between the magnetizable particles and a surrounding medium, for example a biofilm, are suppressed.

According to an embodiment, superparamagnetic metal oxides or ferrimagnetic metal oxides are used as magnetizable materials. Suitable materials for the magnetizable particles are for example magnetite, maghemite and ferrite.

Ferrimagnetic materials which retain their magnetization after an external magnetic field is switched off are magnetically hard materials. At an atomic level ferrimagnetism is characterized by two opposite magnetic vectors of different sizes, which originate from the spinel structure of these oxidic materials.

Both magnetite ($Fe_3O_4$), and $\gamma$-$Fe_2O_3$ are ferrimagnetic materials. These can be distinguished from ferromagnetic materials by the spinel structure and the oxidic chemistry.

Soft ferrimagnetic materials are particularly preferably used for producing the particulate magnetizable support, as they largely lose their magnetization after the magnetic field is switched off and thus form no agglomerates.

According to a further embodiment superparamagnetic materials, such as for example $\gamma$-$Fe_2O_3$, ground down to the nanoscale, are used. Superparamagnetic materials display no further hysteresis.

According to the invention an active component is immobilized on the particulate magnetizable support. What is meant by an active component has already been explained above.

According to a preferred embodiment the active component is a biocatalytically active system. Such a biocatalytically active system can for example be an enzyme, a microorganism or a cell culture cell or also be formed by constituents of cells, for example vesicles.

Suitable microorganisms can be for example eubacteria, archaeobacteria or fungi. The microorganisms can in each case be provided as monocultures, defined mixed cultures or mixed biocoenoses. They can also be cell culture cells. According to a particularly preferred embodiment the microorganisms are in the form of a biofilm immobilized on the particulate magnetizable support material. The biofilm particularly preferably includes several species of microorganism.

According to a further embodiment, capture molecules can be arranged on the surface of the magnetizable support as active component of the magnetizable aggregate. By a capture molecule is meant compounds which can selectively adsorb other compounds, which for example have groups of a specific structure. Capture molecules can be compounds which have a relatively low molecular weight, preferably a molecular weight of less than 100,000 g/mol, according to a further embodiment less than 10,000 g/mol, according to a further embodiment less than 5,000 g/mol, according to yet a further embodiment less than 1,000 g/mol. Examples of capture molecules with a relatively low molecular weight are for example DNA probes or RNA probes.

However compounds or aggregates with a higher molecular weight can also be used as capture molecule. Polymeric molecules with groups that can form ionic or dipolar bonds are suitable for example. Polyethylene imine is an example of a polymer.

However peptides or proteins with a higher molecular weight can also be used as capture molecule, for example antibodies which have been produced with conventional methods to combat a specific antigen.

The bond between the capture molecule and the adsorbed organic/and or inorganic substrate can for example result from ionic or dipolar interactions. For this, suitable affinity groups which can form ionic or dipolar bonds can be provided on the capture molecule. Amino groups, hydroxy groups, carboxy groups, carbamide groups or also heteroaromatic groups are examples of affinity groups.

The following are for example suitable as capture molecule: DNA capture probes, RNA capture probes, antibodies (IgG), protein A, avidin, streptavidin or proteins with long histidine chains.

The capture molecules are suited to adsorbing for example DNA, RNA, amino acids, peptides, proteins, carbohydrates, fats or substances with a complex structure such as e.g. lipoproteins. Such compounds can then be accumulated with the magnetizable aggregate according to the invention for example from biological liquids. Likewise the magnetizable support which was surface-modified with suitable capture molecules can be used to selectively separate specific compounds, for example proteins, peptides, antibiotics, pharmaceutically active substances, specific target DNA molecules, specific target RNA molecules, signalling substances, hormones, growth factors etc. from biotechnologically produced product mixtures.

According to a further aspect, the invention relates to a method for producing such a magnetizable aggregate, wherein a network former, a magnetizable material and a blowing agent are processed to form a granular material, the granular material is blown to form a particulate magnetizable support and an active component is immobilized on the particulate magnetizable support.

The particulate magnetizable support is produced according to methods as already known for producing foam-glass granular material. Essentially, in the production of the particulate magnetizable support methods are followed as described for example in the published documents US2007/0186587, EP 2 022 768 A2 and US2008/0156038, wherein magnetizable particles are additionally incorporated.

Surprisingly, it has been shown that, in spite of the temperatures prevailing during foaming of the granular material as well as process steps such as for example a grinding of the starting product, the magnetic properties of the magnetizable material are retained, with the result that, even after foaming, the particulate support has magnetic properties and is for example attracted in a magnetic field.

A network former, in particular glass powder, and a magnetizable material, for example a magnetic pigment, which are presented in the form of powders are preferably used as starting material. When for example glass powder is used as network former the glass powder or the magnetizable material can be ground correspondingly finely. The components can be ground individually or together. After grinding, the glass powder and optionally the magnetizable material preferably have an average particle size $D_{50}$ of less than 500 µm, according to an embodiment a diameter in the range of from 1 nm to 400 µm, according to a further embodiment a diameter in the range of from 10 nm to 100 µm.

Preferably, at least a part of the glass powder is ground wet. The magnetizable material can be ground dry or wet. This makes it possible to obtain very small particles sizes. After grinding, the particles of glass powder and the magnetizable material preferably have an average diameter $D_{50}$ in the range of from 1 nm to 200 µm, according to an embodiment in a range of from 10 nm to 100 µm.

The glass powder and magnetizable material can be ground together or separately.

The glass, optionally with added magnetizable material, is preferably ground wet for several hours. The total quantity of the glass or only a proportion of the glass can be ground finely. If only a part of the glass is ground finely, the finely ground glass powder is mixed with more coarsely ground glass powder before granulation. The surface of the glass is broken down by the wet grinding, which makes possible a better mechanical cohesion of the blown granular material. The wet grinding is preferably carried out over a period of at least 3 hours, preferably 4 to 8 hours.

The magnetizable material can already be added to the glass powder before the wet grinding. However, it is also possible to first grind the glass powder to a specific particle size beforehand, then to add the optionally likewise pre-ground, magnetizable material and then to further grind the mixture to the desired fineness.

According to an embodiment of the method, water glass can be added to the glass powder during the wet grinding. The surface of the glass powder is thereby further partially dissolved, with the result that a better bond of the glass particles and thus an increase in the mechanical stability of the granular material are achieved.

Glass powder and magnetizable materials are preferably used in a proportion of from 60 to 90 wt.-% glass powder as well as 10 to 40 wt.-% magnetizable Material, according to a further embodiment in a proportion of from 70 to 85 wt.-% glass powder as well as 15 to 30 wt.-% magnetizable material, as well as according to yet a further embodiment in a proportion of from 75 to 82 wt.-% glass powder as well as 18 to 25 wt.-% magnetizable material, relative to the weight of the mixture of glass powder and magnetizable material.

A blowing agent as well as optionally a binding agent are preferably added to the mixture of glass powder and magnetizable material. Suitable blowing agents are for example sugar, manganese dioxide, soda, sodium nitrate or silicon nitride. The quantity of blowing agent is chosen in accordance with the desired degree of foaming. Inorganic binding agents, for example water glass, and/or organic binding agents, for example sugar or resins can be used as binding agents. The mechanical stability of the unfoamed granular material can be increased by the binding agent.

This mixture is then processed to a granular material with conventional methods, optionally after adding coarsely ground glass powder. For this, the mixture can for example be granulated in a stirrer or a pan granulator. However, it is also possible to process the mixture in a spray dryer to form a fine granular material, which is then processed, for example with addition of water glass, to form a coarser granular material. The granular material is optionally further dried and then blown.

The blowing preferably takes place at temperatures of less than 1,000° C., according to an embodiment at a temperature of less than 900° C. and according to yet a further embodiment in a temperature range of from 550 to 800° C. The granular material can be blown with customary methods. The granular material is preferably blown in a rotary kiln. In order to prevent an agglomeration of the granular material during blowing, the unblown granular material can optionally be powdered beforehand with a suitable release agent, for example with a layer of talc. According to an embodiment, a duration in the range of from 5 minutes to 45 minutes is chosen for the blowing.

The foaming of the granular material is preferably carried out in such a way that the particulate magnetizable support has a density of less than 1.2, preferably in the range of from 0.8 to 1.1 kg/l. The density of the obtained magnetizable particulate support can be set by the reaction conditions or also for example by the proportion of blowing agent or water in the unfoamed granular material.

Superparamagnetic or ferrimagnetic materials can be used as magnetizable material, for example magnetite ($Fe_3O_4$) or $\gamma$-$Fe_2O_3$. Nano-$\gamma$-$Fe_2O_3$ is an example of superparamagnetic particles.

According to an embodiment, the production of the particulate magnetizable support is carried out under inert gas, wherein the foaming particularly preferably takes place under inert gas. This protects the magnetizable material, for example magnetite, from oxidation which would cause it to lose its magnetic properties. If $\gamma$-$Fe_2O_3$ is used as magnetizable material, it was surprisingly found that a protective gas atmosphere is not necessary to still achieve significant magnetizability of the particulate support. This is all the more surprising, as pure $\gamma$-$Fe_2O_3$ is converted to $\alpha$-$Fe_2O_3$ at a temperature of more than 300° C., whereby the ferromagnetism is lost.

According to an embodiment of the method according to the invention, the procedure is as follows:
  mixing glass powder and magnetizable material which preferably comprises one or more ferrimagnetic materials,
  dispersing the mixture to form a first homogeneous pre-mixture,
  mixing at least part of this first pre-mixture with blowing agent, optionally binding agent and water to form a homogeneous slip,
  granulating the slip using the optionally remaining residue of the first pre-mixture to form magnetic foam glass-granular material green bodies, and
  foaming the foam glass-granular material green bodies to form magnetic foam glass-granular material particles at temperatures of 750° C. to 1000° C.

According to a preferred embodiment, the mixture of glass powder and magnetizable material is dispersed wet in order to obtain a first homogeneous pre-mixture. Particularly preferably the mixture of glass powder and magnetizable material is ground wet, with the result that a very small particle size is obtained and the surface of the glass is broken down. For the wet grinding customary mills can be used, for example ball mills.

According to a preferred embodiment, during production of the first pre-mixture the glass powder is used in a proportion of from 65 to 92 wt.-% and the magnetizable material in a proportion of from 8 to 35 wt.-%, relative to the total quantity of glass powder and magnetizable material. A particularly preferred pre-mixture contains approximately 80 wt.-% glass powder and 20 wt.-% magnetizable material.

The proportion ranges of the components of the second pre-mixture preferably lie within the range between 30 and 99 wt.-% for water glass, 0 to 70 wt.-% for water and 1 to 10 wt.-% blowing agent, preferably in the form of sodium nitrate. Particularly preferred ranges are 54 to 56 wt.-% for water glass, 43 to 44 wt.-% for water and 2 to 2.5 wt.-% for the blowing agent.

A water glass with a $SiO_2/Na_2O$ ratio of 1.1 to 4 is preferably used as water glass. The water glass preferably has a solids content in the range of from 40 to 100 wt.-%.

The mass ratio of the first to the second pre-mixture is preferably chosen in the range of from 2:1 to 4:1, further preferably 2.7:1 to 3.0:1.

Preferably, within the otherwise at least predominantly amorphous glass structure the crystalline magnetizable areas of the particulate magnetizable support have the following base phase compositions:

25 to 100 mass-% $\gamma$-$Fe_2O_3$ and $Fe_3O_4$ in total, and
0 to 75 mass-% $\alpha$-$Fe_2O_3$.

The following proportion ranges of the crystalline constituents overall are particularly preferred:

0 to 100, preferably 44 mass-% $\gamma$-$Fe_2O_3$ (maghemite)
0 to 100, preferably 34 mass-% $Fe_3O_4$ (magnetite)
0 to 50, preferably 21 mass-% $\alpha$-$Fe_2O_3$ (hematite)

In a manner known per se the granular material can be dried and classified by screening before the foaming.

According to an embodiment, the particulate magnetizable support can also further be provided with a coating which for example promotes the growth of microorganisms. Such a coating can for example be formed from xanthan. For the coating, compounds are preferably used which for example facilitate the adhesion of cells or microorganisms to the particulate magnetizable support or act as nutrients or growth substances. For example trace elements are suitable.

BRIEF DESCRIPTION OF THE DRAWINGS

The invention is explained in more detail below using examples as well as with reference to the enclosed figures. There are shown in.

DETAILED DESCRIPTION OF THE INVENTION

Description of the Preferred Embodiments of the Invention

Figure 1A:
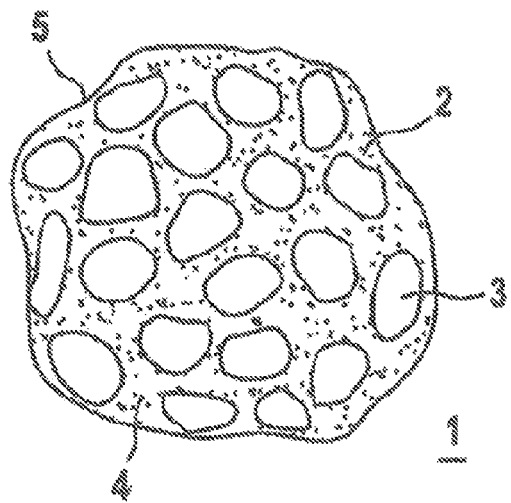
FIGS. 1A and 1B: a diagrammatic representation of sections through various embodiments of a magnetizable support.

FIG. 1A shows diagrammatically a section through a magnetizable support 1, as contained in the magnetizable aggregate according to the invention. The magnetizable support comprises a continuous glass phase 2 which encloses closed pores 3. The closed pores are filled with gas. The density of the magnetizable support 1 can be set by the size and number of the closed pores 3. Distributed in the continuous glass phase 2 are magnetizable particles 4 which form magnetizable areas. The magnetizable particles 4 are embedded and homogeneously distributed in the continuous glass phase. In the embodiment shown in FIG. 1A the outside 5 of the magnetizable support 1 is formed by a continuous skin, with the result that substantially all of the pores 3 are closed.

Figure 1B:
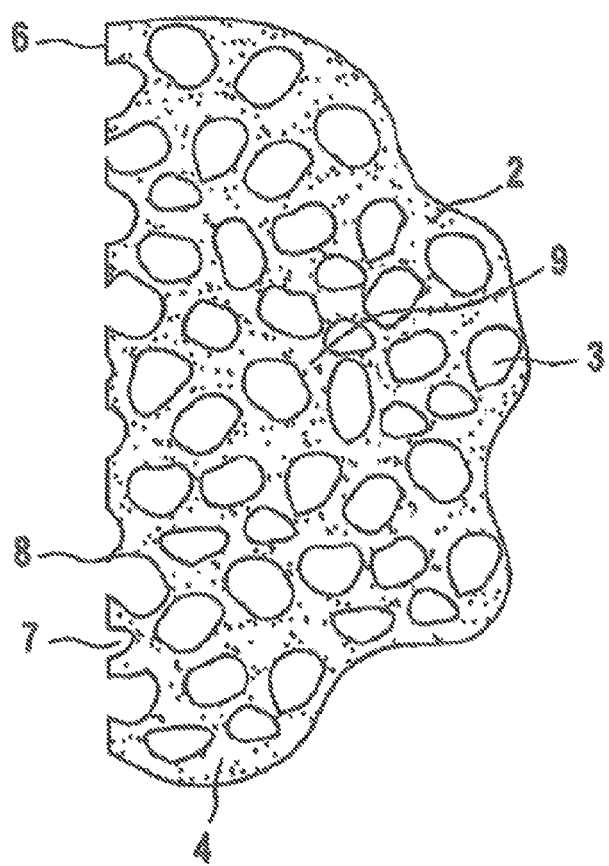

FIG. 1B shows diagrammatically a section through a magnetizable support 1, which is obtained from the magnetizable support shown in FIG. 1a when the latter is broken in a mill for example. The break results in a broken surface 6 on which depressions 7 and ridges 8 are arranged. In the representation chosen in FIG. 1b the broken surface 6 is perpendicular to the section plane with the result that only the edge between broken surface 6 and section plane is shown. Depressions 7 and ridges 8 are obtained when closed pores 3 are opened by the breaking of the magnetizable support 1. As also in the case of the magnetizable support shown in FIG. 1A, the magnetizable support shown in FIG. 1B has in its core 9 a closed-pore foam structure comprising closed pores 3 which are enclosed by the continuous glass phase 2. Magnetizable particles 4, for example ferrite particles, are arranged in the continuous glass phase 2.

FIG. 2 shows various stages passed through during the formation of a biofilm formed from microorganisms on a magnetizable support. The magnetizable support 1 is represented in section in each case.

Figure 2A:
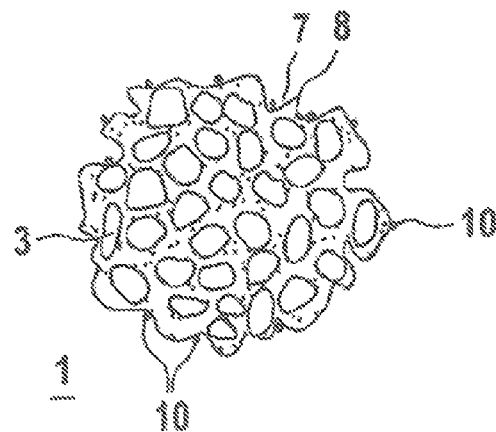
FIGS. 2A to 2C: a diagrammatic representation of various stages that are passed through during the formation of a biofilm on a magnetizable support.

FIG. 2A shows a very early stage of the growth. Microorganisms 10 have become established on individual places on the surface of the magnetizable support 1, wherein the depressions 7 are preferably colonized as protected areas.

Figure 2B:
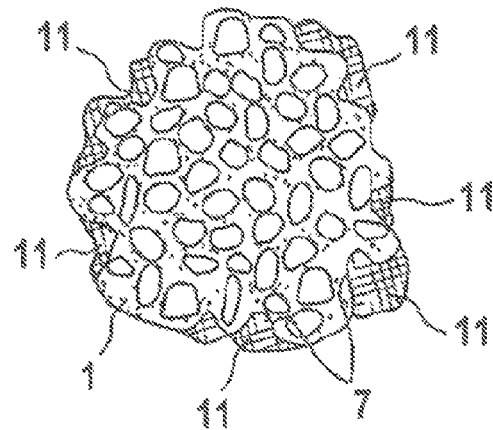

In FIG. 2B the colonization has progressed further. Larger colonies 11 of microorganisms have formed in particular in the depressions 7.

Figure 2C:
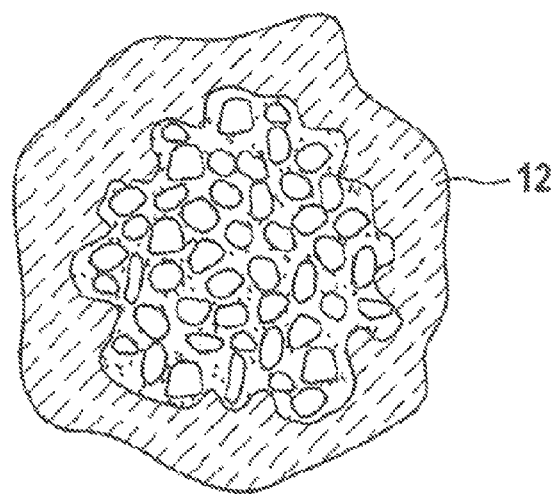

FIG. 2C shows the state after formation of a biofilm 12. The colonies 11 shown in FIG. 2B have grown together and form a continuous biofilm 12. The biofilm 12 comprises several species of microorganism.

FIG. 3 shows diagrammatically various embodiments of the magnetizable aggregate according to the invention. In each case a section through a magnetizable aggregate is represented, wherein, for the sake of clarity, only a part of the section is shown in each case. The magnetizable aggregates in each case comprise a magnetizable support 1, at least the core of which is formed by a closed-pore solid foam. Various active components are arranged on the surface of the magnetizable support.

Figure 3A:
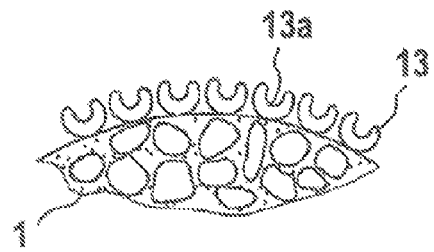
FIGS. 3A to 3H: a diagrammatic representation of various embodiments of the magnetizable aggregate according to the invention.
Figure 3B:
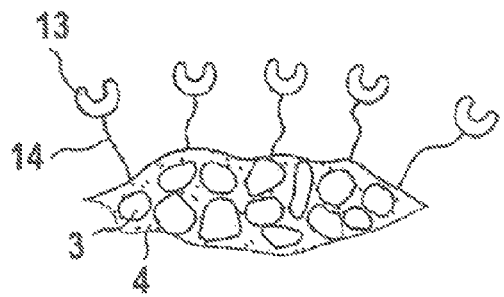
Figure 3C:
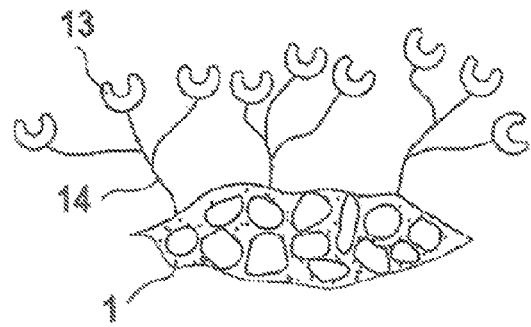

Thus FIG. 3A shows an embodiment in which an enzyme 13 is bound to the surface of the magnetizable support 1. The enzyme has an active centre 13a. The enzyme 13 can also be bound to the surface of the magnetizable support 1 via a spacer 14, as shown in FIG. 3B. The spacer 14 can, as shown in FIG. 3B, be linear or also be branched in order to increase the number of binding sites as shown in FIG. 3C.

Figure 3D:
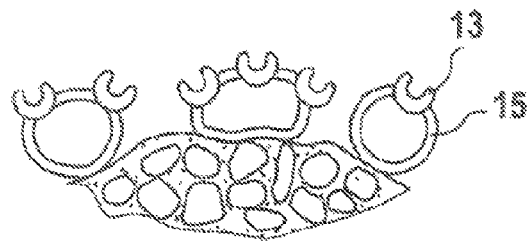

In the embodiment shown in FIG. 3D vesicles 15 are bound as cell constituents to the surface of the magnetizable support 1. Membrane-bound enzymes 13 for example can then be enclosed in the membranes of the vesicles 15.

Figure 3E:
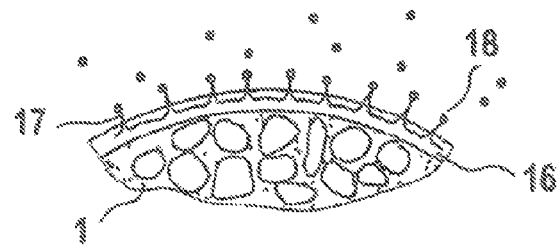

FIG. 3E shows an embodiment in which a polymer film 16 is arranged on the surface of the magnetizable support 1. The polymer film 16 is formed from polymers which have affinity groups 17, for example $NH_3^+$ groups, to which target molecules 18 can be bound. With the embodiment shown in FIG. 3E it is therefore possible to bind target molecules 18 from a liquid phase to the magnetizable aggregate and thereby accumulate them.

Figure 3F:
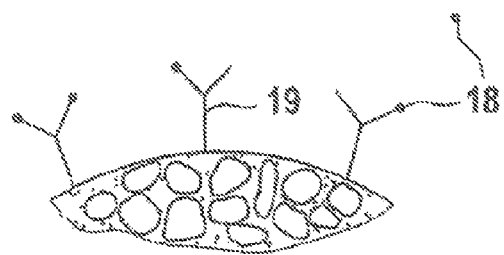

FIG. 3F shows an embodiment in which antibodies 19 are immobilized on the surface of the magnetizable support 1 as capture molecules. The antibodies 19 bind antigens 18 which can thereby be accumulated from a solution.

Figure 3G:
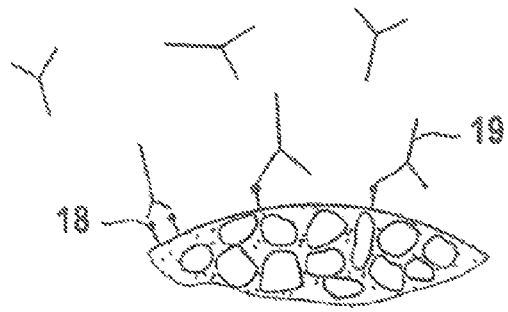

FIG. 3G shows an embodiment in which antigens 18 are immobilized on the surface of the magnetizable support as active component. The antigens 18 act as capture molecules in order to bind antibodies 19 from a solution to the magnetizable aggregate.

Figure 3H:
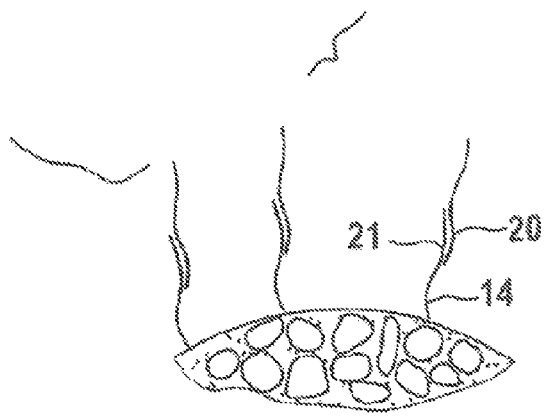

FIG. 3H finally shows an embodiment in which a DNA probe 21 is bound to the surface of the magnetizable support 1 via a spacer 14. Target DNA molecules 20, which have a sequence complementary to the DNA probe, can be bound by the DNA probe and thus accumulated from the solution on the surface of the magnetizable support.

The following methods are used to characterize the magnetizable support.

Water Content:

The water content of the products at 105° C. is ascertained using the DIN/ISO-787/2 method.

Determining the Bulk Density

A measuring cylinder cut off at the 1000-ml mark is weighed. The sample to be examined is then poured in one go into the measuring cylinder by means of a powder funnel such that a bulk mass forms above the top of the measuring cylinder. The bulk mass is wiped off with the help of a ruler which is passed across the opening of the measuring cylinder, and the filled measuring cylinder weighed again. The difference corresponds to the bulk density.

Determining the Particle Bulk Density

The particle bulk density was determined on the basis of DIN EN 13055-1 according to DIN V 18004 5.2 or according to EN 1097-6:2000.

Determining the Magnetic Susceptibility

The magnetic volume susceptibility $c_v$ describes a proportionality constant, defined by the ratio:

$$M = \chi_v \cdot H$$

of magnetization M and magnetic field strength H. As a ratio variable the susceptibility is unitless.

The $c_v$ was determined with an FMA 5000 analyzer from Forgenta (Forgenta Forschungstechnik- and Geräte-Entwicklung Adlershof GmbH, 6, Rudower Chaussee, 12489 Berlin). The apparatus contains a coil with an iron core. An alternating current of 400 Hz flows through it. If a change in the magnetic susceptibility occurs as a result of the introduction of the test material, there will be a change in the inductance and thus the AC resistance in the coil. A bridge circuit enables the measurement of the change in frequency £f. The conversion to $c_v$ takes place according to Klose et al. (2003) [Klose, S; Tölle, R; Bäucker, E; Makeschin, F: "Stratigraphic distribution of lignite-derived atmospheric deposits in forest soils of the upper Lusatian Region, East Germany" Water, Air and Soil Pollution 142:3-25 (2003)] using the following equation:

$$\chi_v = 0.70 \cdot 10^{-5} \cdot \Delta f$$

As magnetizable support particles with varying density are to be compared, instead of $c_v$ the magnetic mass susceptibility $c_{mass}$ is determined. The conversion of $c_v$ to $c_{mass}$ in the SI unit $m^3 \, kg^{-1}$ is carried out using the sample density ρ (kg $m^3$) by means of the equation $$\chi_{mass} = \frac{\chi_V}{\rho}.$$

If samples that had been removed from the fermenter are investigated, these were thickened by adding 0.5% xanthan, in order to prevent the magnetizable support particles from sinking out of the coil during the measurement.

Determining the Viscosity

The flow curves were recorded with the help of the MC1/Rm300 heatable rotational viscosimeter with the Z10 cylinder system from Haake. With this apparatus it is possible to measure the apparent dynamic viscosity of Newtonian and non-Newtonian substances. Here, the substance is situated in an annular gap between two coaxial cylinders. The outer cylinder is stationary, while the inner cylinder is moved. By means of preset programs the resultant shear rate can be set very accurately. This gives rise to a flow resistance in the sample, which represents a measure of the dynamic viscosity of the model liquid. The apparent viscosity can be plotted as a function of the shear rate by a highly accurate torque transducer on the inner cylinder.

EXAMPLE 1

Production of Magnetizable Glass Particles

Method Variant 1

A first method variant for the production of magnetic glass particles provides the following production routine on a laboratory scale:
The following starting materials are used:
glass powder from ground recycled glass: 8028 g
$\gamma\text{-Fe}_2\text{O}_3$ pigment Bayoxide® EAB 21: 1972 g.
These starting materials are pre-mixed dry in a mixer and then ground.
Such pigments are marketed for example by Lanxess. The material
Bayoxide® EAB21 represents an example of the $\gamma$-iron oxide pigment indicated. The material Bayoxide© E 7810 represents an example of a magnetite pigment.
The following are mixed wet as second pre-mixture:
water glass: 1864 g
water: 1480 g
sodium nitrate (blowing agent): 76 g.
The two pre-mixtures are completely granulated in a Lodige ploughshare mixer for 60 seconds. The produced foam glass-granular material green bodies are then dried at a temperature of 105° C. in an oven for several hours.
The dried green bodies are then classified by screening, large constituents mechanically reduced and again classified by screening. A screen limit is 0.25 mm.
The obtained green bodies are foamed with an addition of 30 volume-% kaolin as release agent in a rotary kiln at temperatures between 780° C. and 815° C. over a period of 15 minutes. Depending on the foaming temperature this results in bulk densities in the range between 100 g/l and 1200 g/l, wherein as a rule the bulk density falls as the foaming temperature rises.
The foamed particles of the thus-produced magnetic foam-glass granular material are then again classified by screening and used in a size of from 0.1 mm to 0.3 mm for the application tests described further below.
By means of X-ray diffraction analysis in a diffractometer (Philips X-PERT) the phases of this material can be determined semi-quantitatively at:
40% $\gamma\text{-Fe}_2\text{O}_3$ (maghemite)
24% $\text{Fe}_3\text{O}_4$ (magnetite)
10% $\alpha\text{-Fe}_2\text{O}_3$
17% $\text{SiO}_2$ (cristobalite)
9% $\text{SiO}_2$ (quartz).
The results relative to iron oxide are:
54% $\gamma\text{-Fe}_2\text{O}_3$ (maghemite)
32% $\text{Fe}_3\text{O}_4$ (magnetite)
14% $\alpha\text{-Fe}_2\text{O}_3$
For this material, a dimensionless volume-related susceptibility of $1.21*10^{-5}$ and a mass-related magnetic susceptibility of $2*10^{-8}$ m$^3$/kg were measured as magnetic susceptibility.
The values of the starting oxide Bayoxide® EAB21 are $2.41*10^{-4}$ for the volume-related magnetic susceptibility and $2.77*10^{-7}$ m$^3$/kg for the mass-related magnetic susceptibility. The phase composition is 97% $\gamma\text{-Fe}_2\text{O}_3$ (maghemite) and 3% $\alpha\text{-Fe}_2\text{O}_3$.

Method Variant 2

A second method variant for producing magnetic foam-glass granular material provides for the production of a first pre-mixture from the following constituents:
glass powder: 138.3 g
$\gamma\text{-Fe}_2\text{O}_3$ magnetic particles Bayoxide® EAB 21: 34.6 g.
These constituents are dispersed dry in a mixer.
A second pre-mixture is produced from:
water glass: 137.0 g
water: 108.7 g
sodium nitrate (blowing agent): 5.9 g.
These constituents are dispersed in a mixer to produce a homogeneous slip, which is heated.
A further batch of the first pre-mixture is produced from:
glass powder: 443.2 g
$\gamma\text{-Fe}_2\text{O}_3$ magnetic particles Bayoxide® EAB 21: 118.8 g.
This second batch is also dispersed dry in a mixer.
The two batches of pre-mixture 1 and pre-mixture 2 are granulated in a Hobart mixer with the stages 1-2-1. The thus-produced foam glass-granular material green bodies are dried at a temperature of 105° C. for several hours.
In order to produce the actual magnetizable foam glass-granular material particles, the above-named green bodies are foamed with 30 volume-% kaolin as release agent in a rotary kiln at 740° C. over a period of 0.5 hours. This results in a magnetic foam-glass granular material with a bulk density of 505 g/l.

Method Variant 3

In a third method variant for producing magnetizable foam-glass granular material a spray tower is used for granulation of a slip suspension.
In order to produce this, a first pre-mixture is produced from the following components:
glass powder: 1690 g
$\gamma\text{-Fe}_2\text{O}_3$ magnetic particles: 450 g.
These components are ground and homogenized in a ball mill for approximately 20 min.
The slip suspension is then produced from:
the abovementioned pre-mixture 1900 g
water glass: 600 g
water 1300 g
sodium nitrate (blowing agent) 66g.
These components are dispersed in a mixer to produce a homogeneous slip which is sprayed in a spray tower by means of a ring nozzle.

EXAMPLE 2

Separation Tests with Uncolonized Magnetizable Support Particles

Figure 4:
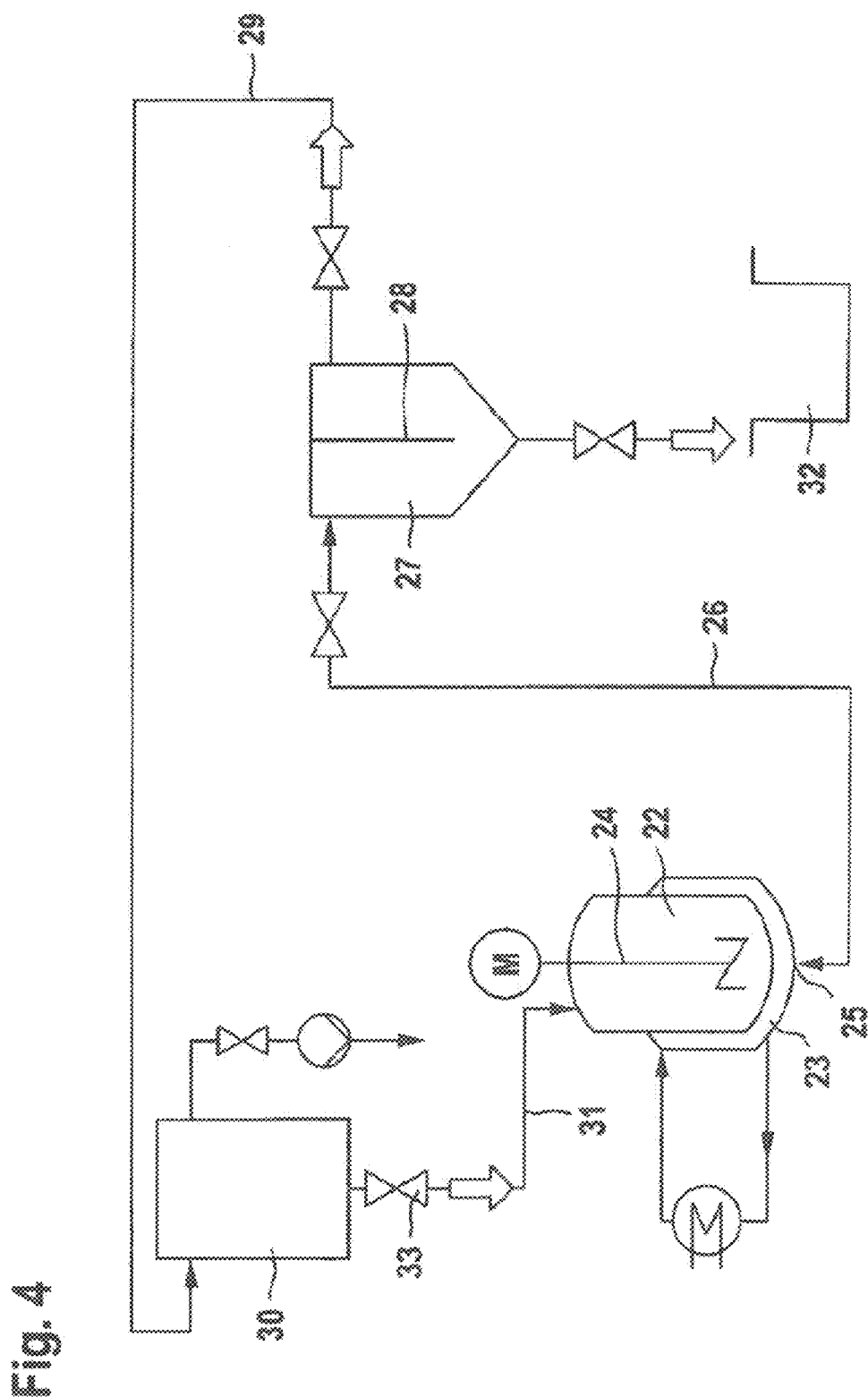
FIG. 4: a diagrammatic representation of a test arrangement for investigating the separation of magnetizable support particles from a model liquid.

The equipment shown in FIG. 4 was used to carry out the separation tests.
A substrate mixture is placed in an agitated tank reactor 22 equipped with a heater 23 and a stirrer 24. Magnetizable supports on which microorganisms have grown are suspended in the substrate mixture. The substrate mixture is discharged out of the reactor via an outlet 25 and transferred via line 26 into a magnetic separator 27. A magnetic separation device 28, for example a rod-shaped magnet, is arranged in the magnetic separator 27. While the substrate mixture is passed through the magnetic separator 27, the magnetizable supports are deposited on the magnetic separation device 28. The substrate depleted of the magnetizable support particles is then passed via a line 29 to a reservoir 30. From the reservoir 30 the substrate can be returned again via line 31 to the agitated tank reactor 22.

The magnetizable supports deposited on the magnetic separation device can be rinsed out and collected in an outlet tank 32.

The model liquid and the magnetizable supports suspended therein are poured into the reservoir 30. The model liquid and the magnetizable supports suspended therein are transferred into the agitated tank reactor 22 by opening the valve 33. The valve 33 is then closed again. The model liquid and the magnetizable supports suspended therein are then pumped out of the agitated tank reactor through the magnetic separator 27, where a separation of the magnetizable supports takes place using the magnetic separation device 28. The model liquid depleted of magnetizable support particles is then pumped back into the reservoir 30 again.

Magnetizable Support Particles

The foam-glass granular materials listed in Table 1 were used as magnetizable support particles:

TABLE 1

Foam-glass granular materials used

| Test product name | Diameter | Magnetic mass susceptibility $\chi_{mass}$ |
|---|---|---|
| V1 | 0.1 to 0.3 mm | $2.00 * 10^{-8}$ m³ kg⁻¹ |
| V2 | 1 to 2 mm | $1.05 * 10^{-8}$ m³ kg⁻¹ |

Model Liquids

Water or mixtures of water and xanthan containing 0.1% or 0.25% xanthan were used as model liquids. Xanthan is a bacterial heteropolysaccharide which is approved for use as a thickening and gelling agent for food production. Aqueous liquids of different viscosity were thus produced. It was thus possible to investigate the influence of viscosity on the recovery of the magnetizable support particles.

Water has the lowest viscosity. 0.1% xanthan solution possesses an average viscosity (approximately in the mid-range of high/medium/low-viscosity reactor discharge). And 0.25% xanthan solution has the highest viscosity.

Various discharges from laboratory biogas reactors were also investigated as examples of actual substrates resulting from the practical implementation of biogas production.

The "meso" seed discharge serves as an example of a high-viscosity discharge. This discharge has the highest dry substance content of the discharges investigated.

The "beet silage" discharge was investigated as an example of a medium-viscosity biogas reactor discharge.

The "AFR discharge thermo" discharge has a dry substance content of only 0.36% and serves as an example of a very low-viscosity discharge.

Determining the Viscosity of the Model Liquids

Figure 5:
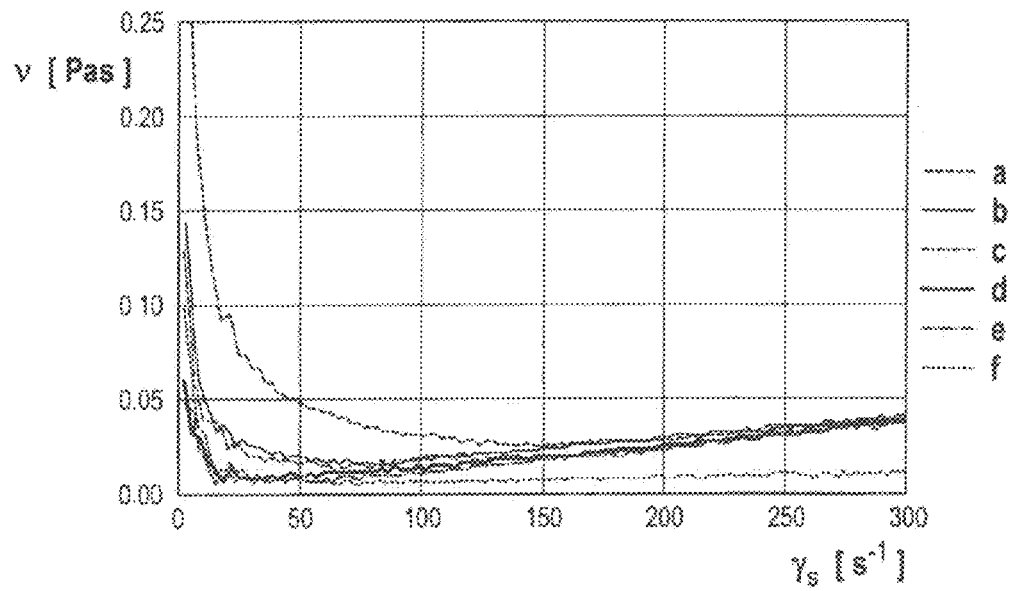
FIG. 5: a diagram in which the apparent viscosity v of various model liquids is plotted as a function of the shear rate $\gamma S$.

As the viscosity has a substantial influence, the model liquids a to f described in Table 2 were precisely set and characterized. In each case the apparent viscosity v in Pas was determined as a function of the shear rate γS in s⁻¹. These data are shown in FIG. 5. For better evaluation, the viscosity of actual reactor discharges was also determined and likewise included in FIG. 5. The indices "room", "meso" and "thermo" relate to the temperatures of the model liquids studied.
room=room temperature (20° C.),
meso=mesophilic (35° C.),
thermo=thermophilic (55° C.)

The viscosity of the model liquids listed in Table 2 was determined.

TABLE 2

Model liquids for determining viscosity

| | Short name for model liquid | Description |
|---|---|---|
| a | xanthan 2.5:1000 room | 0.25% xanthan solution in water |
| b | seed discharge meso | laboratory biogas plant discharge from the mesophilic fermentation of liquid manure (cattle and pig) and silage from renewable raw materials (whole grass, maize and cereal plants) |
| c | xanthan 1:1000 room | 0.1% xanthan solution in water |
| d | fodder sugar beet silage thermo | laboratory biogas plant discharge from thermophilically fermented fodder sugar beet silage with 5% by mass rye grain |
| e | AFR discharge thermo | Laboratory biogas plant discharge from the thermophilic fermentation of predominantly maize silage and small quantities of liquid pig manure. |
| f | water | water |

Test Set-Up

A Liquimag LM9-E-050-7 magnetic separator from S+S Separation and Sorting Technology GmbH, Regener Straβe 130, 94513 Schönberg (2009) was used as magnetic separation device. This device is a filter magnet customary in the trade, which is used in the food industry for separating out metallic impurities. The operating principle is based on the fact that the liquid containing the magnetic particles flows around the magnetic rods arranged one behind the other, and the magnetizable support particles adhere to these rods. Liquid flow and magnetic rods collide in this case, as the magnetic rods are arranged perpendicular to the flow direction.

This magnetic separator must be cleaned manually at specific time intervals. To do this, it is necessary to stop the liquid circulation and remove the magnetic rods.

The magnetic separator was connected to a reservoir and a collection container as shown in FIG. 4, in order to pass the samples through the magnetic separator. The sample material was conveyed by means of negative pressure which is produced by a pump connected to the collection container. In addition the sample temperature, the mass of the sample pumped into the collection container and the throughflow time are determined.

Test Procedure:

A mixture was produced for each test from the respective model liquid a to f and a specific quantity of magnetizable support particles. The viscosity of the model liquid and its content of magnetizable support particles were systematically varied.

This mixture was then poured into the reservoir and pumped through the magnetic separator with a likewise varied flow velocity. The pumping process was carried out by means of negative pressure at the collection container. The mass of the magnetizable support particles retained in the magnetic separator was determined at the end, and from this the recovery percentage calculated relative to the mass of magnetizable support particles originally added to the sample.

For this, after each separation test the stainless steel casings of the magnetic rods of the magnetic separator were cleaned manually. This means that the magnetizable support particles adhering to the stainless steel casings were rinsed off with deionized water and collected in evaporating dishes.

The liquid was then evaporated in a drying cupboard at 105° C. over a period of 24 h. The weight of the separated magnetizable support particles could thus be determined after subtracting the empty weight of the evaporating dish.

Test Results

Figure 6:
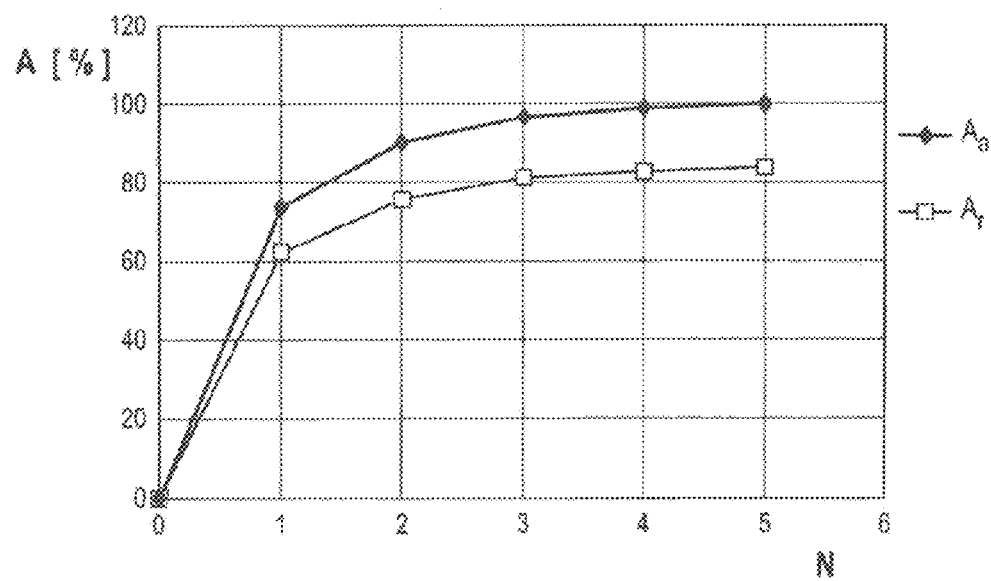
FIG. 6: a diagram representing the degree of separation A of magnetizable support particles as a function of the frequency N of passes through a magnetic separation device, wherein water was used as model liquid.

1. Degree of Separation of the Magnetizable Support Particles in the Magnetic Separator 1.1. Water 1% (w/w) magnetizable support particles with a diameter of 0.1-0.3 mm (V1) were suspended in water and passed 20 times through the magnetic separator. After the 1st, 2nd, 5th, 10th and 20th pass the magnetizable support particles separated in the magnetic separator were collected, dried and weighed. The separated quantity of magnetizable support is given in Table 3. The values result in the separation curve represented in FIG. 6, wherein the degree of separation A is given for each sample number N. Shown in each case is the degree of separation $A_a$ relative to the quantity of magnetic support used as well as the degree of separation $A_r$ relative to the total quantity of magnetically separated support.

TABLE 3

Quantity of the magnetizable support particles separated from water; quantity of magnetic support used 70.00 g; maximum separated quantity 58.87 g; 84.1%

| Pass | Sample no. N | Quantity per pass (g) | Total | Proportion of quantity separated $A_r$ (%) | Proportion of quantity used $A_a$ (%) |
|---|---|---|---|---|---|
| 0 | 0 | 0 | 0 | 0.0 | 0.0 |
| 1 | 1 | 43.68 | 43.68 | 74.20 | 62.40 |
| 2 | 2 | 9.46 | 53.14 | 90.27 | 75.91 |
| 2-5 | 3 | 3.77 | 56.91 | 96.66 | 81.29 |
| 6-10 | 4 | 1.44 | 58.34 | 99.10 | 83.35 |
| 11-20 | 5 | 0.52 | 58.87 | 100.00 | 84.10 |

After 20 passes the curve exhibited saturation behaviour, i.e. after 20 passes practically all the separable magnetizable support particles were separated out of the model liquid. Of the 70.00 g of magnetizable support particles measured out at the start of the test, it was possible to separate 58.87 g. This corresponds to 84.10%. The remaining proportion of 15.9% constitutes poorly separable or non-separable material with only weak magnetic properties. The separable 84.10% of the quantity of magnetizable support particles originally used was set as the maximum separable proportion of the magnetizable support particles and thus as reference value for 100%. Thus calculated, after the 1st pass it was possible to separate 74.20% of the separable material, after the 2nd pass a further 16.07% and for separation of the remaining 9.63% a further 18 passes were required.

Aqueous Xanthan Solution (0.25%)

Figure 7:
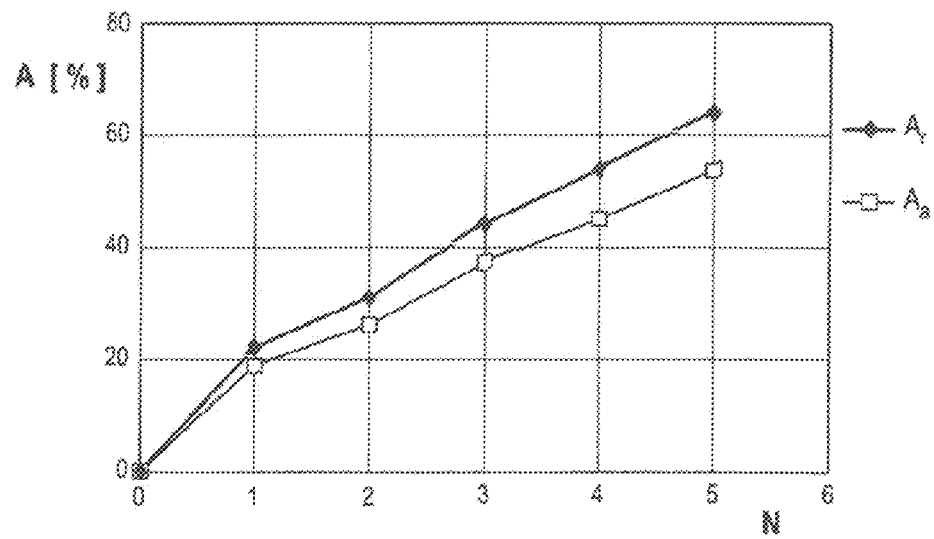
FIG. 7: a diagram representing the degree of separation A of magnetizable support particles as a function of the frequency N of passes through a magnetic separation device, wherein a 0.25% solution of xanthan in water was used as model liquid.

The test was repeated with 0.25% aqueous xanthan solution. The quantity of separated magnetic support particles is given in Table 4. The degree of separation of the magnetizable support particles is shown in FIG. 7. Given in each case is the degree of separation $A_a$ ascertained for the sample number N listed in Table 4, which relates to the quantity of magnetic support used, and the degree of separation $A_r$ which relates to the magnetically separable quantity of the magnetic support.

TABLE 4

Quantity of the magnetizable support particles separated out of a xanthan solution (0.25%); quantity of magnetic support used 70.00 g; maximum separated quantity 58.87 g; 84.1%

| Pass | Sample no. N | Quantity per pass (g) | Total (g) | Proportion of separated quantity $A_r$ (%) | Proportion of used quantity $A_a$ (%) |
|---|---|---|---|---|---|
| 0 | 0 | 0 | 0 | 0.0 | 0.0 |
| 1 | 1 | 13.05 | 13.05 | 22.17 | 18.64 |
| 2 | 2 | 5.27 | 18.32 | 31.12 | 26.17 |
| 2-5 | 3 | 7.66 | 25.98 | 44.13 | 37.11 |
| 6-10 | 4 | 5.76 | 31.74 | 53.92 | 45.34 |
| 11-20 | 5 | 5.73 | 37.47 | 63.65 | 53.53 |

Only a total of 63.65% of the magnetically separable particles (100%) were separated after 20 passes. After the 1st pass the figure was only 22.17%; after the 2nd pass a further 8.95%. The increased viscosity significantly impairs the separation of the 0.1-0.3 mm magnetizable support particles.

Figure 8:
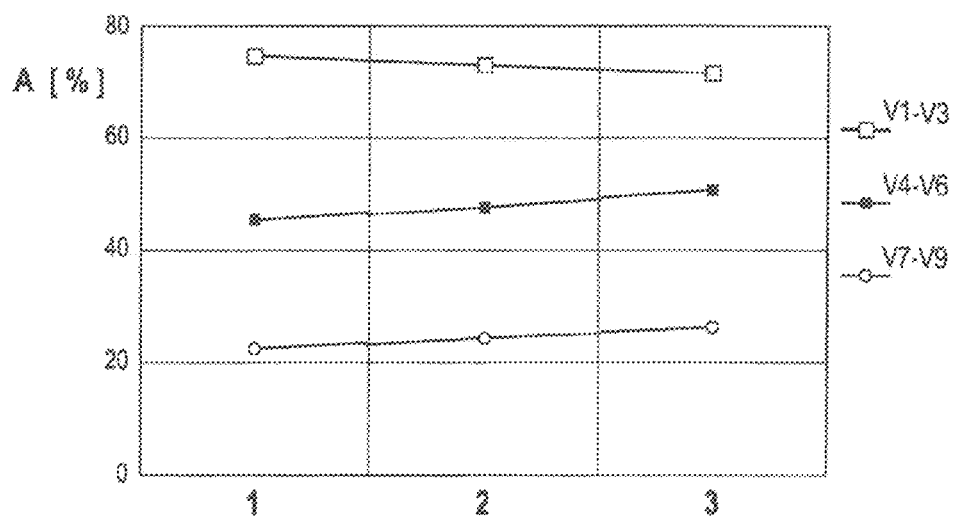
FIG. 8: a diagram representing the degree of separation A of magnetizable support particles in the case of a single pass through a magnetic separation device, wherein the proportion of the magnetizable support particles in the sample as well as the viscosity of the model liquid were varied.

Influence of the viscosity of the model liquid and the concentration of the magnetizable support particles on the degree of separation The model liquid with the magnetizable support particles suspended therein was pumped through the magnetic separator once only. The model liquids used and the quantity and type of the magnetizable support particles are listed in Table 5 and represented by graph in FIG. 8. Column 1 gives the degree of separation A for a quantity of 0.1% magnetizable support, column 2 the degree of separation A for a quantity of 0.5% magnetizable support and column 3 the degree of separation A for a quantity of 1.0% magnetizable support.

TABLE 5

Model liquids and separation rate for a single pass of the sample (V1) through the magnetic separator

| Test no. | Model liquid | Support concentration (wt.-%) | Degree of separation (%) |
|---|---|---|---|
| 1 | water | 0.1 | 75.08 |
| 2 | water | 0.5 | 71.75 |
| 3 | water | 1.0 | 72.80 |
| 4 | xanthan (0.1%) | 0.1 | 45.01 |
| 5 | xanthan (0.1%) | 0.5 | 47.90 |
| 6 | xanthan (0.1%) | 1.0 | 50.55 |
| 7 | xanthan (0.25%) | 0.1 | 23.10 |
| 8 | xanthan (0.25%) | 0.5 | 22.80 |
| 9 | xanthan (0.25%) | 1.0 | 26.95 |

With only one separation and an increase in the mass concentration of magnetic particles (0.1-0.3 mm) from 0.1% to 0.5% and 1% the degree of separation changed only slightly.

It would have been expected that with an increasing particle mass the particles in the separator would obstruct and shield one another. Clearly, the mass concentration range of 0.1-1% was so small that the expected effect did not yet occur.

On the other hand the increase in viscosity had a clear effect: the higher the viscosity, the lower the degree of separation.

Figure 9:
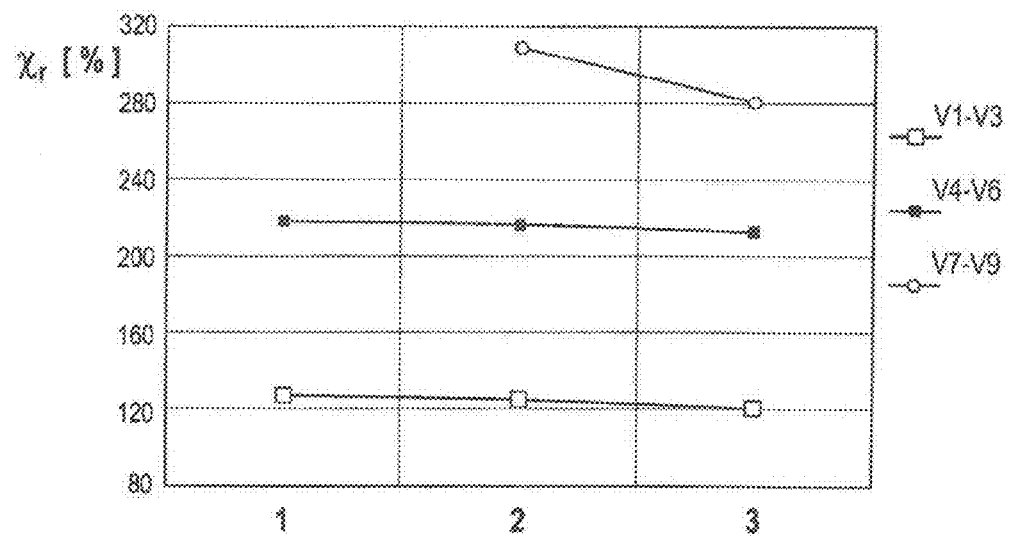
FIG. 9: a diagram representing the relative magnetic susceptibility $\chi_x$ of the magnetizable support particles, wherein only the support particles deposited in the magnetic separation device were measured.

The magnetic susceptibility of the magnetizable support particles separated in each case was measured and related to the magnetic susceptibility of the starting material (100%). The higher the viscosity of the model liquid (and the fewer the magnetizable support particles separated), the higher also the magnetic susceptibility of the separated magnetizable support particles. Accordingly a high viscosity of the model liquid is selective of particles with high magnetic susceptibility (in each case with 0.1-0.3 mm particle diameter). The relative magnetic susceptibility $\chi_r$ measured for the separated magnetizable support particles is listed in Table 6 for the various tests and represented by graph in FIG. 9. For the various model liquids column 1 gives the relative magnetic susceptibility $\chi_r$ for a quantity of 0.1% magnetizable support, column 2 the relative magnetic susceptibility $\chi_r$ for a quantity of 0.5% magnetizable support and column 3 the relative magnetic susceptibility $\chi_r$ for a quantity of 1.0% magnetizable support.

TABLE 6

Relative magnetic susceptibility $\chi_r$ of the magnetizable support particles separated for a single pass of the sample (V1) through the magnetic separator

| Test no. | Model liquid | Support concentration (wt.-%) | Relative magnetic susceptibility $\chi_r$ (%) |
|---|---|---|---|
| 1 | water | 0.1 | 124.95 |
| 2 | water | 0.5 | 128.22 |
| 3 | water | 1.0 | 120.31 |
| 4 | xanthan (0.1%) | 0.1 | 215.13 |
| 5 | xanthan (0.1%) | 0.5 | 219.76 |
| 6 | xanthan (0.1%) | 1.0 | 209.84 |
| 7 | xanthan (0.25%) | 0.1 | n.c. |
| 8 | xanthan (0.25%) | 0.5 | 308.57 |
| 9 | xanthan (0.25%) | 1.0 | 282.79 |

2. Effect of the Volume Flow on the Degree of Separation

Figure 10:
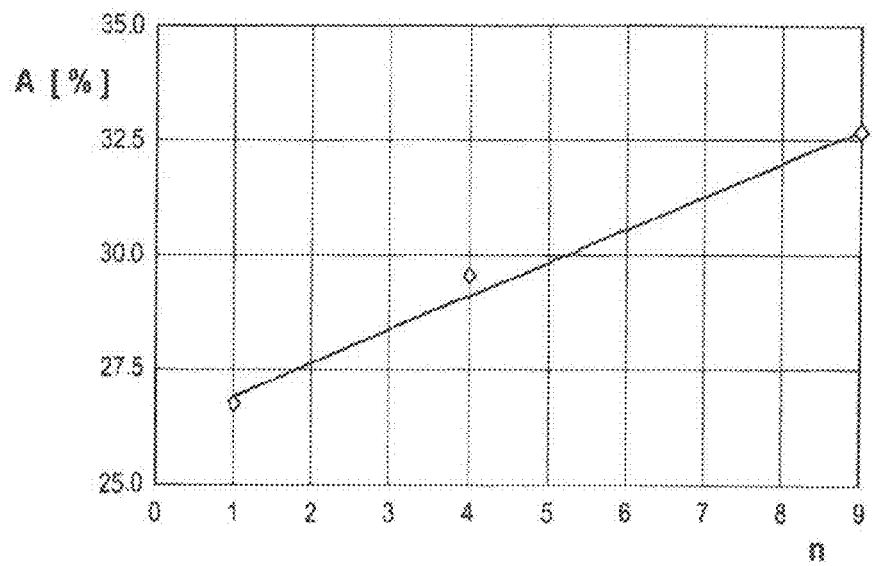
FIG. 10: a diagram representing the degree of separation A as a function of the volume flow in the magnetic separation device, given as the number n of passes through the separation device.

The degree of separation A of the magnetizable support particles in an aqueous 0.25% xanthan solution for a single pass through the magnetic separator was measured. The results are listed in Table 7 and reproduced by graph in FIG. 10.

TABLE 7

Degree of separation of magnetizable support particles out of xanthan/water 2.5:1000 for several passes through a separator

| Number of passes n | Degree of separation A (%) |
|---|---|
| 1 | 27.0 |
| 4 | 29.3 |
| 9 | 32.5 |

The higher the volume flow (i.e. the higher the flow velocity in the magnetic separator), the lower the degree of separation of the magnetizable support particles.

Figure 11:
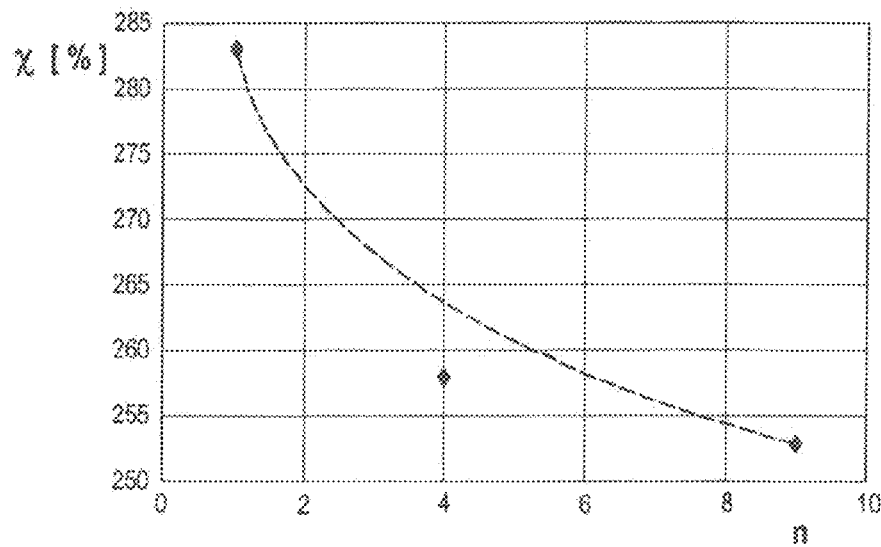
FIG. 11: a diagram representing the magnetic susceptibility $\chi$ of the magnetizable support particles separated in the magnetic separation device as a function of the volume flow, given as the number n of passes through the separator.

The magnetic susceptibility of the separated magnetizable support particles was also determined. The results are summarized in Table 8 and reproduced by graph in FIG. 11.

TABLE 8

Magnetic susceptibility of the support particles separated out of an aqueous xanthan solution (0.25%) relative to the number of passes through a separator

| Number of passes | Magnetic susceptibility $\chi$ in % relative to the susceptibility of the support particles originally used |
|---|---|
| 1 | 283 |
| 4 | 258 |
| 9 | 256 |

The higher the volume flow in the magnetic separator, the higher the magnetic susceptibility of the separated magnetizable support particles.

The explanation given by the inventors for this effect is that only magnetizable support particles with high magnetic susceptibility are acted on by magnetic forces sufficiently high to be able to separate them despite the strong flow.

3. Effect of Particle Size and Viscosity on the Degree of Separation

Figure 12:
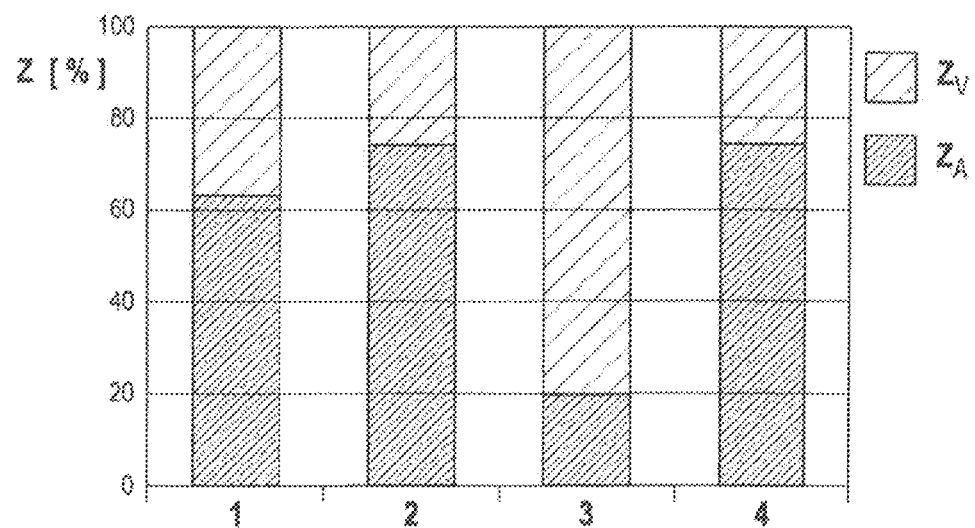
FIG. 12: a diagram representing the influence of the particle size and the viscosity of the test liquid on the degree of separation.

Magnetizable support particles with a particle size of 1-2 mm (V2) were compared with magnetizable support particles with a particle size of 0.1-0.3 mm (V1). The lowest mass concentration of 0.1% was chosen. Water and 0.25% aqueous xanthan solution were used as model liquids. Measurements were carried out at a constant volume flow of 30 l/min. The results are listed in Table 9 and FIG. 12.

TABLE 9

Influence of particle size in the case of separation with 0.1 mass-% magnetizable support particles

| No. | Particle fraction | Medium | Separated proportion $Z_a$ [%] | Loss $Z_v$ [%] |
|---|---|---|---|---|
| 1 | 0.1-0.3 mm | water | 63.14 | 36.86 |
| 2 | 1-2 mm | water | 74.14 | 25.86 |
| 3 | 0.1-0.3 mm | xanthan 2.5:1000 | 19.43 | 80.57 |
| 4 | 1-2 mm | xanthan 2.5:1000 | 74.43 | 25.57 |

Although the degree of separation dropped dramatically (from 63% to 19%) in the case of a particle size of 0.1-0.3 mm due to the increase in viscosity, it remained almost uninfluenced (74% and 74%) in the case of a particle size of 1-2 mm despite an increase in viscosity. Explanation: the particle volume increases along with the particle diameter. The magnetic force acting on the particles thereby increases (provided there is a constantly high proportion of magnetically susceptible material mixed in.) The increased magnetic force is then sufficient to overcome the increased friction forces in the highly viscous medium.

Figure 13:
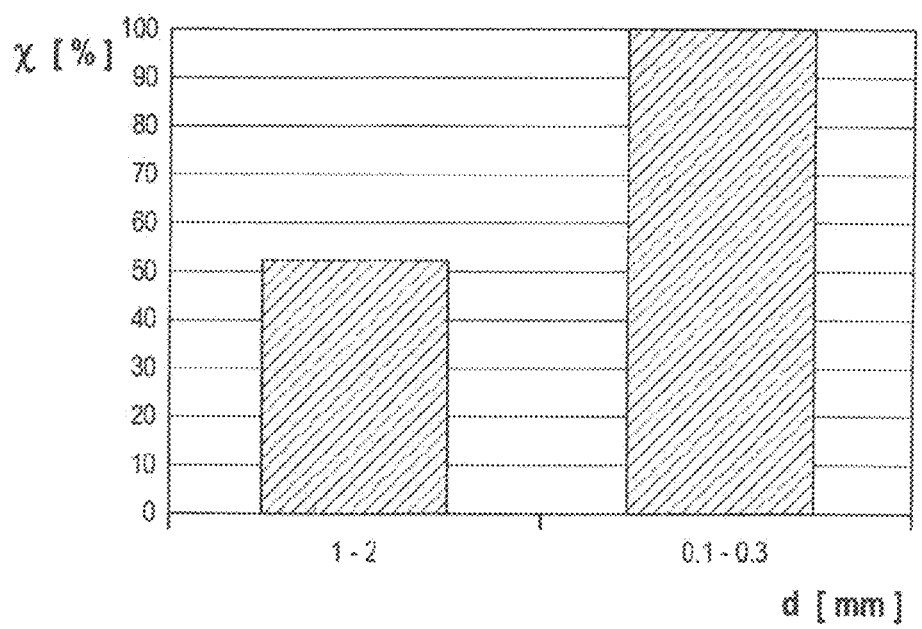
FIG. 13: a diagram representing the influence of the particle size on the magnetic susceptibility $\chi$.

Furthermore, the magnetic susceptibility of both types of magnetizable support particles used in the tests was investigated. The results are reproduced in Table 10 and by graph in FIG. 13.

TABLE 10

Influence of particle size on magnetic susceptibility

| Magnetic susceptibility $\chi$ [%] | Particle diameter d |
|---|---|
| 52.38 | 1-2 mm |
| 100 | 0.1-0.3 mm |

Although both granulations had been produced from the same mixture of magnetic pigment and glass powder (i.e. they should theoretically contain the same proportion of magnetizable material) and a particle size fractionation was carried out by means of screening, the particle size 0.1-0.3 mm had almost twice as high a magnetic susceptibility as the particle size 1-2 mm. It is unclear whether this is a function of the particle size, or whether mixing/unmixing phenomena during production are involved.

EXAMPLE 3

Fermentation of Beet Silage in 50-Liter Fermenters with the Aid of Magnetizable Support Particles In order to clarify whether the fermentation of beet silage to biogas can be increased by using microorganisms immobilized on magnetizable support particles, two identically constructed agitated tank fermenters which differed in only two features were operated in parallel with an operating volume of 50 liters each. At the start of the test, 1 percent by mass magnetizable support particles was added to the "magnetic fermenter" (hereafter abbreviated to MF). In order to be able to separate the magnetizable support particles out of the discharge again and recycle it, a magnetic separator was incorporated into the MF outlet. No magnetizable support particles were added to the "control fermenter" (hereafter abbreviated to MFC) and no magnetic separator was installed in its outlet. The operating method of both fermenters was, so far as possible, designed to be identical during the approximately seven-month test period.

Material and Methods

Test Set-Up

Figure 14:
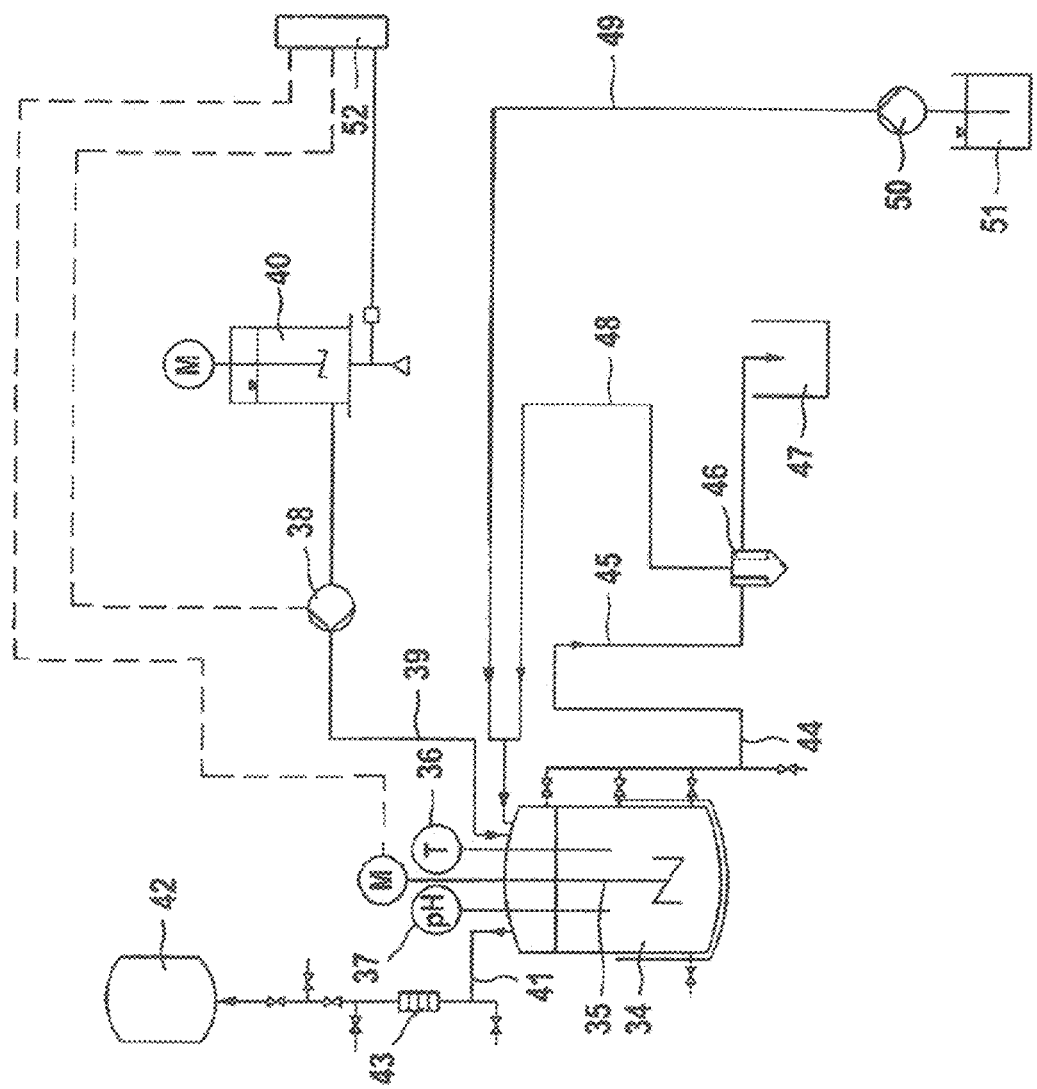
FIG. 14: a diagrammatic representation of the test set-up for fermenting beet silage.

FIG. 14 shows diagrammatically the test arrangement set-up.

A temperature-controlled fermenter 34 which is equipped with a stirrer 35, and probes for measuring the temperature 36 and pH 37 can be charged with the help of a metering pump 38 via line 39 with substrate taken from a substrate reservoir 40. The substrate is fermented in the fermenter 34, wherein the gases released during fermentation collect in the headspace of the fermenter 34 and are transferred from there via line 41 into a gas collecting container 42. The quantity of gas can be measured via gas meter 43. Spent substrate is fed to a discharge hopper 45 via line 44. In the case of the "magnetic fermenter MF" a magnetic separation device 46 is additionally arranged to which the spent substrate from the discharge hopper 45 is fed. A separation of the magnetizable support particles with the microorganisms that have grown thereon takes place in the magnetic separation device 46. The depleted substrate is then fed to a digestate container 47. The magnetizable particles separated out of the spent substrate can be returned via line 48 to the fermenter 34 again. Furthermore, water from the water storage tank 51 can be fed to the fermenter 34 via line 49 with the help of the dosing pump 50. The substrate feed to the fermenter 34 can be controlled with the help of a control device 52.

In the case of the control fermenter "MFC" the spent substrate was fed directly to the digestate container 47.

Magnetizable Support Particles

In order to carryout the tests, the magnetizable support particles produced as described in Example 1 with a particle size of 0.1-0.3 mm were used.

Magnetic Separator

Liguimag LM9-E-050-7. Manufacturer S+S Separation and Sorting Technology GmbH, Regener Straße 130, 94513 Schönberg (2009).

Substrate

Beet silage that had been reduced with a mincer was used as substrate.

Seeding Material

For seeding, digested seed slurry from another fermentation reactor was used.

Auxiliary Materials

Solution of trace elements, N-containing solution with $NH_4HCO_3 \cdot NH_4COONH_2$, S-containing solution with $Na_2SO_4$ to overcome deficiencies.

Analytical Methods

In order to implement the parameters observed during the test, the following devices and methods were used:
Quantity of gas: drum-type gas meter TG 05; Ritter Apparatebau,
Biogas composition: multichannel measuring device SSM 6000; Pronova Analysentechnik
Dry substance: gravimetrically by drying to constant weight at 105° C.;
Organic dry substance (ODS): gravimetrically by incineration at 550° C.;
Volatile organic acids and volatile alcohols: determination by gas chromatography using an FID by comparison with retention times of known compounds;
Lactic acid: HPLC with RI detector;
Corrected organic substance=ODS+volatile acids+volatile alcohols+volatile proportion of lactic acid;
Sugar: GC+RI detector;
VOA/TIC (ratio of volatile organic acids to total inorganic carbonates): titration with 0.05 M $H_2SO_4$, Nordmann method;
$NH_4$—N: conversion to $NH_3$, steam distillation, back titration;
$N_{tot}$: DIN EN 25663: 1933-11;
C,N,S content: simultaneous determination with a Vario EL II elemental analyzer;
P content: after breaking down according to DIN EN ISO 15681-2:2005-05;

Microscopy for assessment of the extent and quality of the colonization of the magnetizable support particles: Zeiss Axiostar plus FL microscope, Zeiss AxioCam MRc5 camera, Zeiss AxioVision 4.8 image analysis system. Phase contrast microscopy method (to make the particles and their external outlines visible) and reflected-light fluorescence (1st excitation of the nucleic acid-fluorescence dye SYTO 13 with blue light, emission of green fluorescence; 2nd excitation of the specific cofactors of the methane gas bacteria with UV light, emission of the blue, turquoise, green or yellow autofluorescence in the whole of the visible spectrum). The sampling for the microscopy of the magnetizable particles was carried out once a month. The culture broths of the fermenters were additionally investigated as required.

Test Procedure:

The test duration was divided into 2 test periods.

1st Test Period:

The 1st test period lasted 14 weeks.

At the start of the test (day 0) both fermenters were filled with seed slurry. From day 8 onwards, beet silage was introduced manually into the fermenter. On day 14, in the case of the MF only, 1 wt.-% magnetizable support particles, relative to the total mass of the fermenter content, was added. During the entire, approximately seven-month test duration, no further magnetizable support particles were added thereafter. The reference temperature of the reactors was set at 38.5-39° C. From the start of the fifth week onwards, beet silage was added continuously as substrate, wherein the volume load was gradually increased. The 1st test period served to start up both fermenters.

The magnetizable support particles proved to be mechanically stable during the 1st test period.

A degree of separation of 92% was calculated for the magnetizable support particles. At the end of the 1st test period, of the original 1 percent by mass magnetizable support particles, 0.7% still remained in the MF.

Microscopic analysis showed that the magnetizable support particles were slowly colonized. From month to month the degree of colonization gradually increased, wherein the bacteria first preferred protected areas, i.e. cracks, depressions, sites next to surface elevations of the magnetizable support particles, and only later colonized the exposed surface areas of the magnetizable support particles. Shortly before the end of the 1st test period the best-colonized magnetizable support particles possessed a maximum degree of surface coverage of 50-60%. The majority of the magnetizable support particles had only a thin, patchy growth of individual cells or small cell groups. Filamentous bacteria also occurred in the growth. Completely uncolonized magnetizable support particles were no longer detected. Each magnetizable support particle had at least individual immobilized bacteria on its surface. Blue, turquoise and yellow autofluorescing bacteria were able to be detected between non-autofluorescent bacteria in the growth. This is an indication that part of the growth consisted of the desired methane gas bacteria. Overall there was still so little colonization at the end of the 1st test period that a clear increase in efficiency of the MF compared with the MFC was not yet to be expected.

Efficiency parameters of MF and MFC: quantity of biogas, proportion of methane, methane yield, pH, organic acids and VOA/TIC values were used for the assessment. In the first weeks both fermenters, as expected, behaved in almost identical manner, for which reason there is no representation of this.

2nd Test Period

The 2nd test period lasted approximately 13.5 weeks. The beet silage from the first test period was replaced with fresh beet silage wherein, unlike the first test period, smaller containers were used, with attention being paid from the outset to exclusion of air, and cooling. The beet silage was diluted with water in order to guarantee pumpability. Additionally, water was added to the fermenters in order to be able to make the influence of the magnetizable support particles more clearly visible by the reduced average residence times. Moreover, the separation of the magnetizable support particles was supposed to be facilitated by the reduction in viscosity of the medium. Each fermenter was provided with its own circulation thermostat, so that when the external temperature dropped, the reference temperature was able to be raised to 41° C. in order to suppress any yeast growth. The volume load was carefully increased to approximately 3.5 g OS/(l*d). During the first 9 weeks of the 2nd test period it was possible to reliably remain below concentrations of undissociated acetic acid (2 g/l) or propionic acid (0.7 g/l) regarded as inhibitory.

In the MFC a relatively strong foam formation was observed, which could however be counteracted by more vigorous stirring to destroy the foam. In the MF foam also formed due to the emission of $CO_2$ during the addition of the acid beet silage. This foam was not however as durable as in the MFC. Magnetizable support particles floating in the foam led to a more rapid bursting of the bubbles.

After approximately 7 weeks, stable conditions had become established in the fermenters. The magnetizable support particles continued to be stable. No broken particles could be detected with the naked eye. Small magnetizable support particle splinters could be found grown in individual flocs under a microscope. Inasmuch as the floc, due to the enclosed splinter, can be separated in the magnetic separator, this does not denote any loss of magnetizable support particles or valuable biomass.

The average degree of separation of the magnetizable support particles still only amounted to 33%. A viscous brown foam had formed and sludge which also contained magnetizable support particles had been deposited by sedimentation in the magnetic separator. At the end of the second test period, a content of 0.41 wt.-% magnetizable support particles was measured in the fermenter—this is still only 41% of the 1 wt.-% originally used. These high losses are attributable to a not yet optimized magnetic separator as well as the not yet optimum properties of the magnetizable support particles.

The first microscopic examination, 4 weeks after the start of the 2nd test period, showed that the growth on the magnetizable support particles was maintained despite the numerous changes in the environment and had even increased slightly overall. However, the increase in the immobilized biomass on the magnetizable support particles was clearly less than at all previously investigated intervals.

A microscopic examination approximately 6 weeks after the start of the second test period showed that the colonization of the magnetizable support particles had again increased more markedly. The best-colonized particle had a 90% coverage and a biofilm up to 42 μm thick in places with a pronounced matrix of extracellular polymer substances and contained numerous, intensely yellow autofluorescing methane gas bacteria. The majority of the magnetizable support particles exhibited "crack colonization" or a thin, patchy growth of individual cells, small cell groups and filamentous bacteria. The majority of the magnetizable support particles had a surface coverage of approximately 30%-70%. However magnetizable support particles were also observed which had less growth. Only upon microscopic examination approximately 2 weeks before the end of the 2nd test period could sufficiently well-developed biofilms be detected. The colonization density had clearly increased compared with the previous microscopic examination. In the case of the best-colonized magnetizable support particles, a good 90% of the surface was covered. A clear proportion of the magnetizable support particles had a degree of colonization of approximately 70-90%. The majority of the magnetizable support particles had a degree of colonization of approximately 30%-70% surface coverage. No more magnetizable support particles which exhibited no colonization were observed. The biofilms had increased in thickness and complexity. For the first time highly organized mushroom- or tower-shaped bacteria colonies had formed. The surface-covering, matrix-enclosed, mixed biofilms (with strongly autofluorescent methane gas bacteria) as well as filamentous bacteria had also increased. At the end of the second test period, based on an assessment of the microscopic image, a high-performance biofilm had developed on at least some of the magnetizable support particles.

Figure 15:
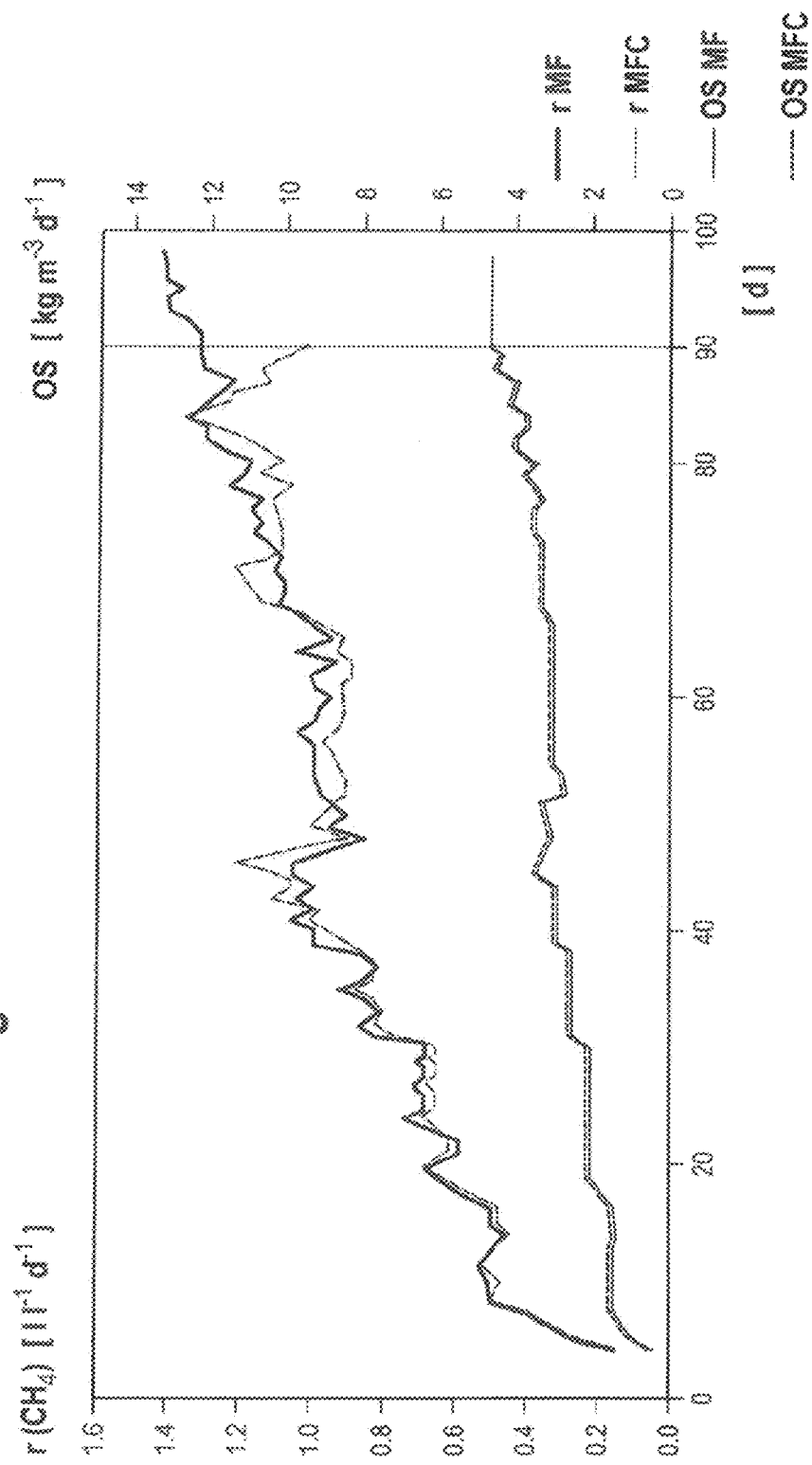
FIG. 15: a diagram in which the methane formation rate $r(CH_4)$ and the organic substance volume load OS of the reactors MF and MFC are plotted as a function of the progress of the test over time. In the case of the control reactor MFC the substrate feed was started approximately 3 months after the start of the 2nd test phase.
Figure 16:
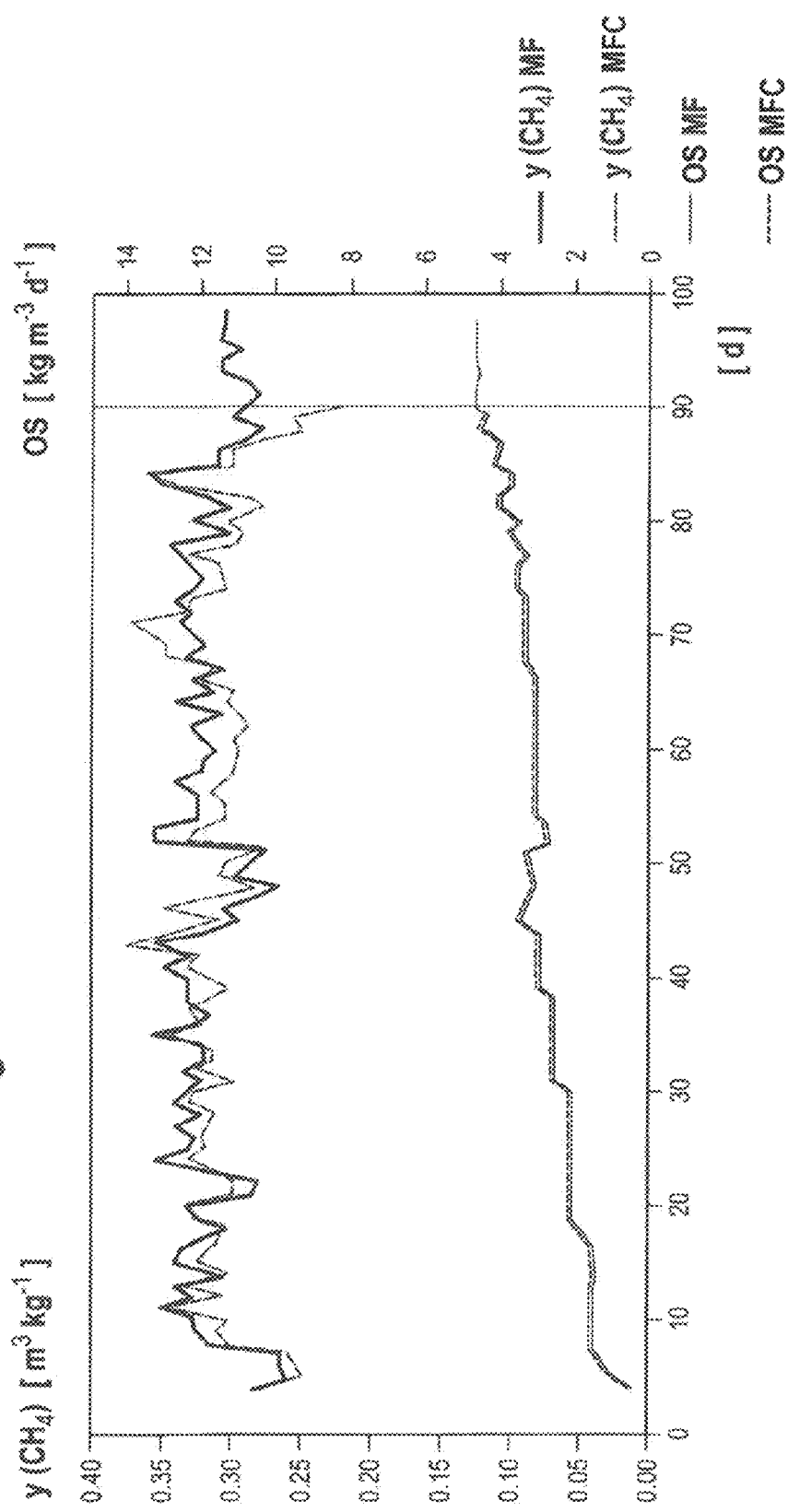
FIG. 16: a diagram in which the methane yield $y(CH_4)$ and the organic substance volume load OS of the reactors MF and MFC are plotted as a function of the progress of the test over time. In the case of the control reactor MFC the substrate feed was started approximately 3 months after the start of the 2nd test phase.
Figure 17:
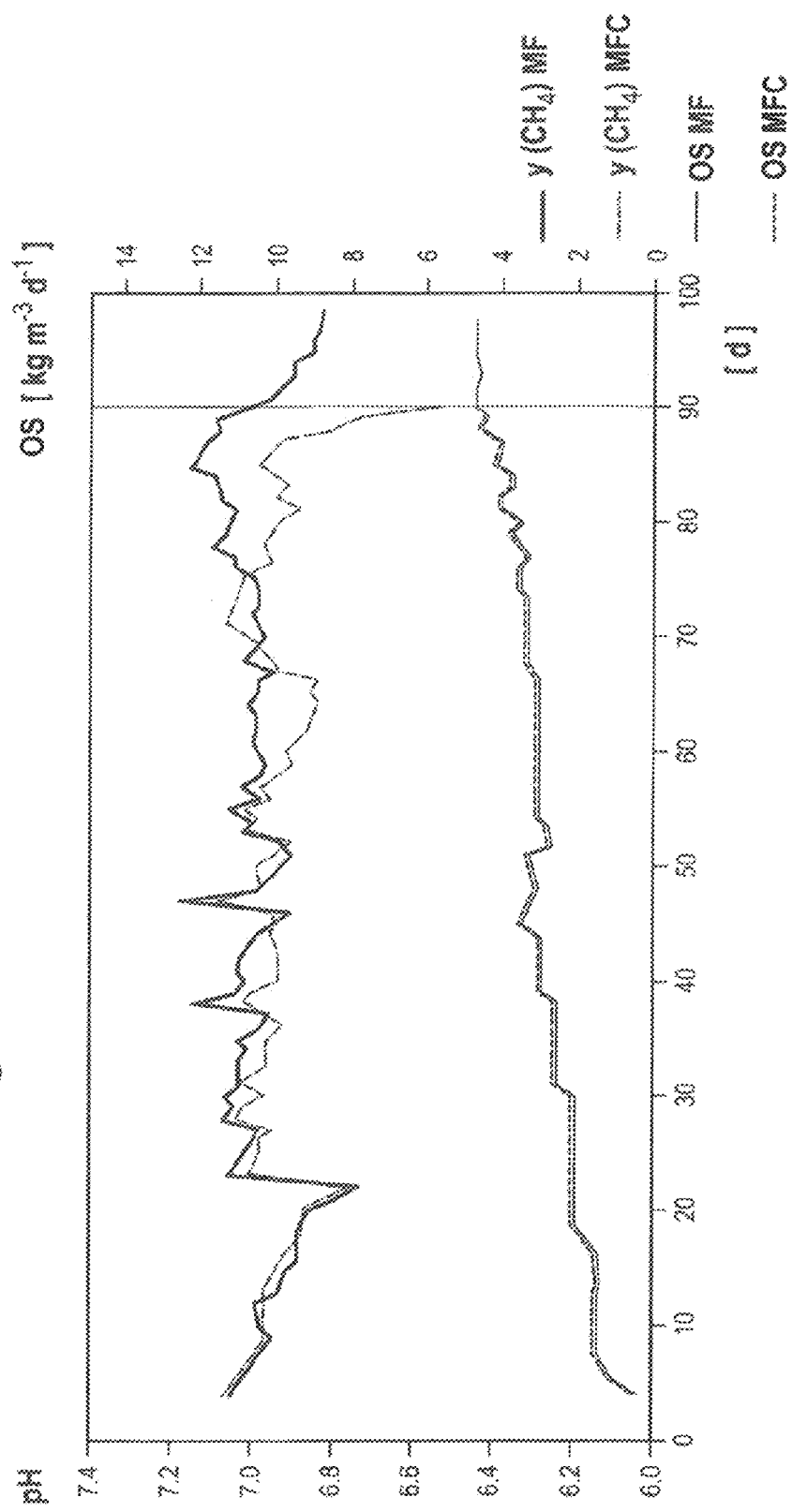
FIG. 17: a diagram in which the pH of the substrate in the reactor and the organic substance volume load OS of the reactors MF and MFC are plotted as a function of the progress of the test over time. In the case of the control reactor MFC the substrate feed was started approximately 3 months after the start of the 2nd test phase.

FIGS. 15 to 17 show methane formation rate [$r(CH_4)$], methane yield [$y(CH_4)$] and pH relative to the volume load [OS] throughout the whole 2nd test period for the reactors MF and MFC. The volume load was gradually (step-wise) increased. Methane formation rate and methane yield proceeded very similarly in both reactors over a long period. As expected, the methane formation rose as the volume load increased. The methane yield fluctuated by a value of a good 0.3 m³ of methane per kg of organic substance, wherein peak values of 0.36 (MF) and 0.37 (MFC) were reached.

Approximately two months after the start of the 2nd test period and with a volume load of 3 kg m$^{-3}$ d$^{-1}$ up to the end of the third month of testing in the 2nd test period, the tendency emerged for both the methane formation rate and also the methane yield of the MF, with few exceptions, to be slightly higher than in the case of the MFC.

Clear differences could be discerned only at higher volume loads. Once the volume load increased to 4.17 kg m$^{-3}$ d$^{-1}$ the MFC values dropped sharply. In order to avoid irreversible process overloading, the MFC substrate addition was started a good three months after the test began. At this point in time, the methane formation rate and the methane yield of the MFC were more than 20% lower than those of the MF.

A comparison with the development of the pH values demonstrates the biological instability of the MFC. Hydrolyzing, acidogenic and acetogenic bacteria reduce the pH by their metabolic activity and make the substrates ($H_2$, $CO_2$, acetate etc.) available to the methanogenic bacteria. The methanogenic bacteria at the end of the metabolic chain metabolize these low-molecular substances and increase the pH by their metabolic activity. In fermenters with mixed biocoenoses of the 4 named groups of bacteria, pH values of between 7 and 8 are usually established at equilibrium. A pH of 6.7 is regarded as the lower limit value for an undisturbed methane formation process. Below a pH of 6.7 the proportion of the protonated, volatile organic acids is so high that the undissociated organic acids inhibit the methane bacteria. An inhibition of the methanogenic bacteria leads to a reduced elimination of acidity or to a reduced formation of alkalinity. The pH is thereby further reduced, whereby the inhibitory effect of the volatile organic acids on the methanogenic bacteria increases and a vicious circle sets in which, unless countermeasures are taken, can lead to the complete breakdown of the system.

Under stable operating conditions, a pH of 7.0 or slightly higher had been established in MF and MFC. Even from a volume load of approximately 3.5 kg m$^{-3}$ d$^{-1}$ onwards, the pH of the MFC began to gradually drop, which can be regarded as a sign of slight, slow overloading. With a further increase of the volume load to approximately 4 kg m$^{-3}$ d$^{-1}$ the pH rapidly dropped to 6.52. The test reactor with the magnetizable support particles (MF) tolerated this load increase much better. Volume loads of approximately 3.5 kg m$^{-3}$ d$^{-1}$ and slightly more did not bring about a gradual reduction in the pH, instead the pH remained stable or even gradually increased slightly. At volume loads of above 4 kg m$^{-3}$ d$^{-1}$ although there was initially also a fall in the methane yield and a reduction in the pH in the MF, the reactor recovered again. The pH asymptotically approached a lower limit value. It can therefore be assumed that the MF became biologically stable and continuous operation could be continued with this volume load.

The observed differences can be explained as follows: from a specific volume load onwards, the washing-out rate in the MFC exceeds the growth rate of the slow-growing methane gas bacteria, with the result that these were flushed out with the discharge. The other, more rapidly growing bacteria groups (acid-forming), however, were able to remain in the system, with the result that there was a gradual fall in pH, with all the consequences thereof. On the other hand, in the MF the methane gas bacteria immobilized on the magnetizable support particles were returned to the fermenter, with the result that at a volume load of 4.17 kg m$^{-3}$ d$^{-1}$ there was still no lack of methane gas bacteria.

The concentrations of volatile fatty acids make it possible to draw additional conclusions about process stability. The concentrations of free fatty acids substantially confirm the conclusions already drawn from methane formation, methane yield and pH. Thus the acid concentrations in the reactor content of the MFC at higher volume loads were much higher than those in the MF.

EXAMPLE 4

Screening Tests for Examination of Various Magnetic Supports

Simple screening tests were carried out with different magnetizable support particles made of a foam glass in order to investigate the influence of various factors on the formation of a biofilm.

Test Procedure:

The tests, lasting approximately 4 months, were carried out in a climatic chamber at 39° C. Fermenting balloons made of PE with a nominal volume of 30 l, which were connected to gas collecting bags, served as bioreactors. The nominal filling volume amounted to 15 l. At the start of the test 14 l of boiled tap water adjusted with dithionite as a reducing agent was introduced in each case. Then 500 ml of magnetizable particles was added in each case. In the control batch without magnetizable particles, a corresponding volume of water was added. Seeding was then carried out with approximately 500 ml of seeding material. In order to guarantee as great as possible a variety of microorganisms, in particular methane gas bacteria and primary colonizers, the seed material originated from 3 different sources. Seeding was carried out again with higher volume loads on 2 subsequent occasions. Sugar beet silage served as substrate. The volume load was slowly increased linearly (from 0.0 to 1.0 g ODS/(l*d) over 90 days). At the end a maximum volume load of approximately 1.1 g ODS/(l*d) was reached.

The descriptions of the magnetizable supports used for the tests are listed in Table 11.

TABLE 11

Description of the magnetizable supports

| No. | magnetizable support |
|---|---|
| 1 | magnetic foam glass, spray particle, 0.1-0.3 mm D |
| 2 | magnetic foam glass, broken particle, 0.25-1.5 mm D |
| 3 | magnetic foam glass, broken particle 0.25-1.5 mm D, coated with xanthan |
| 4 | magnetic foam glass, broken particle 0.25-1.5 mm D, coated with xanthan and trace elements |
| 5 | magnetic foam glass, broken particle 0.25-1.5 mm D, coated with gelatin |
| 6 | magnetic foam glass, broken particle 0.25-1.5 mm D, with inorganic chemical surface modification |
| 7 | magnetic foam glass, broken particle 0.25-1.5 mm D, reducing melted granulation |
| 8 | magnetic foam glass, broken particle 0.25-1.5 mm D, alternative blowing agent |
| 9 | $Fe_2O_3$ granular material pure, unblown |
| 10 | foam glass from series production, from magnetic separator, 0.5-1.0 mm D |
| 11 | reference without magnetic particles |

Analysis:

The extent of the colonization was investigated by fluorescence microscopy and photographically documented (6 sampling dates). The assessment was carried out subjectively based on visual impression. Redox potential, pH and VOA/TIC values were determined for the process control. The fermentation gas volume formed was determined by estimating the expansion of the gas collecting bags. The gas composition was analyzed using random samples.

Results:

The most important results are listed in Table 11:

The quantity of fermentation gas volume was determined by estimating the filling level of the gas collecting bag and divided into categories 0, +, ++.

The proportion of methane in the biogas was determined 4 weeks after seeding in each case.

The colonization of the magnetizable supports was determined using light microscope images and divided into categories 0, +, ++, +++ and ++++. 0 denotes no colonization and ++++ the formation of a largely continuous biofilm.

TABLE 11

Summary of the screening-test results

| No. | Fermentation gas volume | Proportion of methane [*] | Effects | Colonization, |
|---|---|---|---|---|
| 1 | + | 49.9 | Flotation tendency | + |
| 2 | ++ | 45.3 | Sedimentation tendency | ++ |
| 3 | ++ | Not determined | Sedimentation tendency | +++ |
| 4 | ++ | 49.7 | Sedimentation tendency | ++++ |
| 5 | +, much leakage | Not determined | Sedimentation tendency | +++ |
| 6 | + | Not determined | Sedimentation tendency | +++ |
| 7 | ++ | Not determined | Sedimentation tendency | ++(+) |
| 8 | ++ | 51.8 | Sedimentation tendency | ++++ |
| 9 | Test discontinued after a few weeks due to decomposition of the granular material | 48.7 | $Fe_2O_3$ was reduced to FeS. The granular material decomposed to very finely distributed, black, completely unmagnetic FeS. Positive: $H_2S$ formation was suppressed. | Not applicable |
| 10 | ++ | Not determined | Best distribution in the culture broth; suspension | ++ |
| 11 | Leakage over several weeks | Not determined | Not applicable | Not applicable |

Gas analysis of random samples shows that a methane gas fermentation in fact took place.

At the maximum volume load of 1.1 g ODS/l(*d) reached, theoretically 12.9 standard liters of biogas/d would have been expected. The highest value of approximately 12 l biogas/d (not standardized) reached in practice shows that the substrate was largely converted. The pH and VOA/TIC values at the end of the test period lay within a good range (pH 7-8 and VOA/TIC<0.3, often in the range between 0.2 and 0.3 regarded as optimum).

Colonization: a few hours after seeding, reversible adhesion could already be observed. In the course of 12 weeks after the seeding the extent of colonization in all samples (apart from batch 9) gradually increased. After 12 weeks the biofilms were best pronounced in all samples. Those samples designated ++++ were particularly positive. Surprisingly the reducing melted granulation delivered results just as good as the oxidizing melted granulations.

Figure 18:
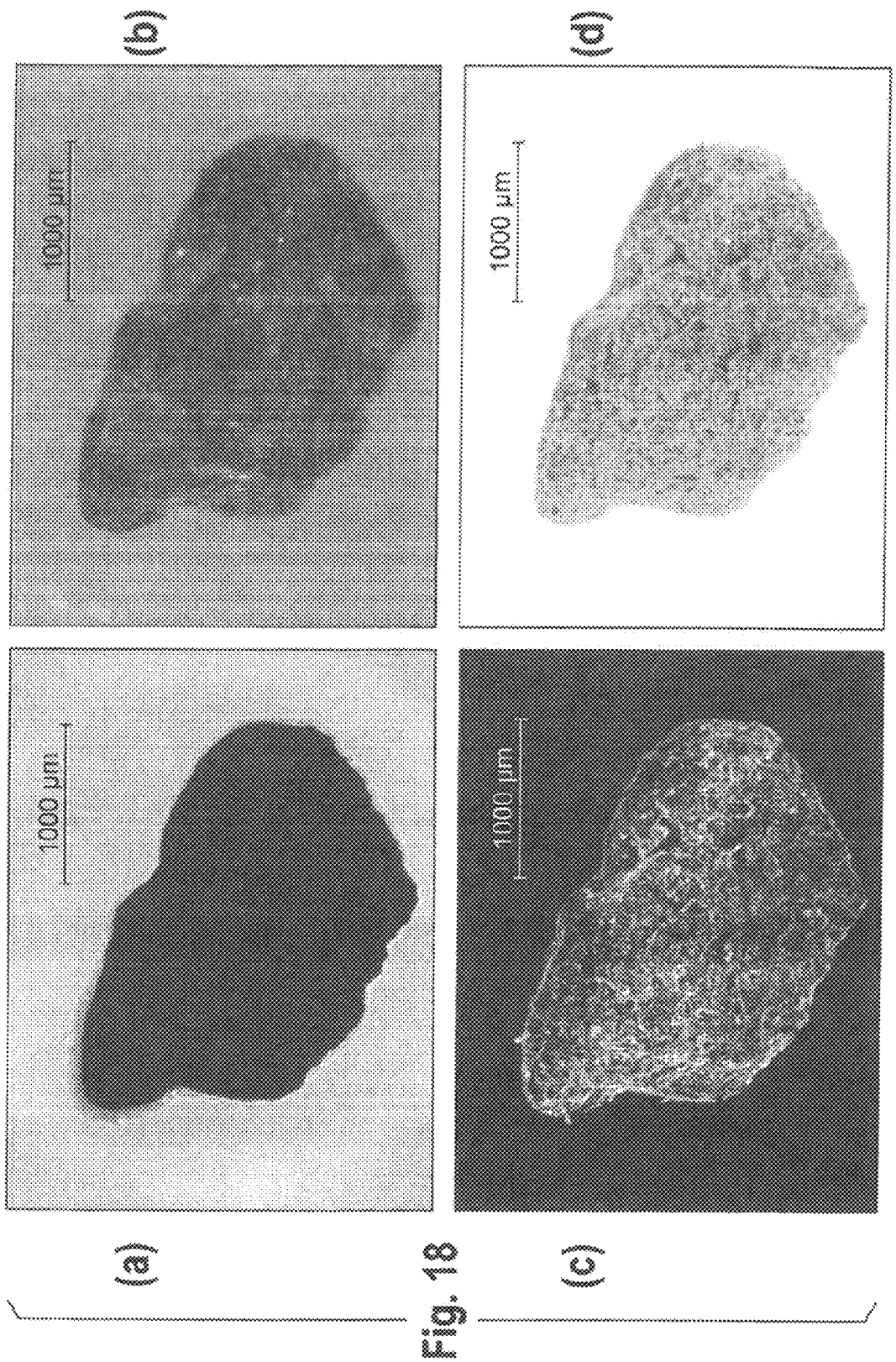
FIG. 18: light microscope images of a magnetizable particulate support particle which is covered with a biofilm; there are shown in (a) a phase contrast image, (b) a reflected-light fluorescence with UV excitation and emission over the whole visible spectrum; (c) a reflected-light fluorescence with blue excitation and emission in the green region and (d) a mixed image of images (a) to (c).

FIG. 18 shows light microscope images of an individual large magnetic foam glass particle (sample 4, coated with xanthan and trace elements) after a 12-week incubation period. FIG. 18A shows a single image which was taken using the phase contrast method. The external outlines of the dark particle can be recognized. The suggestion of a biofilm enclosing the particles can be recognized around the outline. Three colonies protruding from the particle are particularly striking.

FIG. 18B shows a single image which was taken using the reflected-light fluorescence method. UV excitation was used and emission was recorded over the whole of the visible spectrum. Extremely brightly fluorescing cellulose fibres and cellulose-containing plant parts can be recognized. These display a bright blue fluorescence in the original images. Areas appearing somewhat less bright, which fluoresced intensively blue, intensively yellow or turquoise or greenish in the original image, correspond to colonies of methane gas bacteria. Areas appearing dimly bright, which fluoresced matt blue in the original image, correspond to extracellular polymer substances of the bacteria colonies with their inclusions. These form the cloudy light places on the surface of the magnetic particle. The background fluorescence (autofluorescences of microscope slide, cover slip, buffer and substances dissolved or very finely distributed therein etc.) is considerable and makes the background look grey or blue-grey in the original image and not deep black. The magnetic foam glass particle possesses absolutely no autofluorescence, with the result that uncolonized or only thinly colonized places appear black.

FIG. 18C shows a reflected-light fluorescence image with blue excitation and emission in the green region, which can be recognized as bright areas in the image. The image is calculated from a z-stack and therefore shows an extended depth of field. Coloration with a nucleic acid fluorescence dye makes DNA and RNA fluoresce intensely green, with the result that all the microorganisms in the biofilm are clearly visible. The magnetic foam glass particle was colonized all around. The biofilm covers almost the whole surface, but still very thinly. Only in the area of depressions and pores are there only a few bacteria.

FIG. 18D shows a mixed image of the 3 previous channels (addition of A+B+C).

| List of references |
|---|
| 1 magnetizable support |
| 2 continuous glass phase |
| 3 closed pore |
| 4 magnetic particle |
| 5 outside |
| 6 broken surface |
| 7 depression |
| 8 ridge |
| 9 core |
| 10 microorganism |
| 11 colony |
| 12 biofilm |
| 13 enzyme |
| 14 spacer |
| 15 vesicle |
| 16 polymer layer |
| 17 affinity group |
| 18 target molecule |
| 19 antibody |
| 20 DNA probe |
| 21 target DNA sequence |
| 22 agitated tank reactor |
| 23 heater |

-continued

List of references 24 stirrer
25 outlet
26 line
27 magnetic separator
28 magnetic separation device
29 line
30 reservoir
31 line
32 outlet tank
33 valve
34 fermenter
35 stirrer
36 thermometer
37 pH meter
38 dosing pump
39 line
40 substrate reservoir
41 line
42 gas collecting container
43 gas meter
44 line
45 discharge hopper
46 magnetic separator
47 digestate container
48 line
49 line
50 dosing pump
51 water collection container
52 control device

What is claimed is:

1. A method for treating an organic and/or inorganic substrate comprising:
 (a) providing a substrate mixture which contains the organic and/or inorganic substrate in a reaction chamber;
 (b) adding a magnetizable aggregate to the substrate mixture, wherein the magnetizable aggregate comprises (i) a magnetizable support and (ii) an active component immobilized on the magnetizable support;
 (c) converting the substrate mixture to a product mixture with the magnetizable aggregate; and
 (d) separating the magnetizable aggregate from the product mixture with a magnetic separation device, wherein the magnetizable support is present in the form of a particulate magnetizable support, wherein the particulate magnetizable support has a core and is constructed from a solid foam having a continuous phase which surrounds pores of the solid foam, wherein magnetizable areas are arranged in the continuous phase, and wherein the solid foam is closed-pore at least in the core of the magnetizable support.

2. The method according to claim 1, further comprising transferring the product mixture into a magnetic separation device in which the magnetizable aggregate is separated off from the product mixture.

3. The method according to claim 1, further comprising returning the magnetizable aggregate separated off from the product mixture to the reaction chamber.

4. The method according to claim 1, wherein the active component is a biocatalytically active system.

5. The method according to claim 4, wherein the biocatalytically active system comprises at least one microorganism.

6. The method according to claim 5, further comprising providing the at least one microorganism in the form of a biofilm.

7. The method according to claim 1, wherein the particulate magnetizable support has ridges and depressions on its surface.

8. The method according to claim 1, wherein the continuous phase of the particulate magnetizable support is formed from an inorganic material.

9. The method according to claim 8, wherein the inorganic material is a glass.

10. The method according to claim 1, wherein the particulate magnetizable support has a magnetic mass susceptibility in the range of from $5 \times 10^{-9}$ to $3.7 \times 10^{-7}$ m$^3$/kg.

11. The method according to claim 5, further comprising carrying out the conversion of the substrate mixture by the at least one microorganism to a product mixture under anaerobic conditions.

* * * * *

UNITED STATES PATENT AND TRADEMARK OFFICE
CERTIFICATE OF CORRECTION

PATENT NO. : 8,637,300 B2
APPLICATION NO. : 13/763331
DATED : January 28, 2014
INVENTOR(S) : F. Ruf et al.

It is certified that error appears in the above-identified patent and that said Letters Patent is hereby corrected as shown below:

In the Specification

In Column 32:
Line 33: delete "and" and insert -- und -- therefor.
Line 39: delete "Abridge" and insert -- A bridge -- therefor.
Line 40: delete "£f." and insert -- Δf. -- therefor.
Line 51: delete "(kg m$^3$)" and insert -- (kg m$^{-3}$) -- therefor.

In Column 33:
Line 26: delete "Bayoxide©" and insert -- Bayoxide® -- therefor.
Line 33: delete "Lodige" and insert -- Lödige -- therefor.

In Column 41:
Line 50: delete "Liguimag" and insert -- Liquimag -- therefor.

In Column 42:
Line 10: delete "R1" and insert -- RI -- therefor.
Lines 14 and 15: delete "volatile organic acids to total inorganic carbonates)" and insert -- volatile organic acids to total inorganic carbonates) -- therefor.

In Column 47:
Line 4: delete "methane [*)" and insert -- methane [%] -- therefor.

Signed and Sealed this
Eighth Day of July, 2014

Michelle K. Lee
*Deputy Director of the United States Patent and Trademark Office*